(12) United States Patent
Kharbanda et al.

(10) Patent No.: US 11,484,507 B2
(45) Date of Patent: Nov. 1, 2022

(54) POLYMERIC NANOPARTICLES PROVIDING NUCLEIC ACIDS ENCODING TNF-α

(71) Applicant: NANOPROTEAGEN, Grand Cayman (KY)

(72) Inventors: Surender Kharbanda, Natick, MA (US); Vasundhara Shukla, Ghaziabad Up (IN); Donald Kufe, Wellesley, MA (US); Harpal Singh, New Delhi (IN)

(73) Assignee: Hillstream BioPharma, Inc., Chester, NJ (US)

( * ) Notice: Subject to any disclaimer, the term of this patent is extended or adjusted under 35 U.S.C. 154(b) by 0 days.

(21) Appl. No.: 16/466,566

(22) PCT Filed: Nov. 1, 2017

(86) PCT No.: PCT/US2017/059542
§ 371 (c)(1),
(2) Date: Jun. 4, 2019

(87) PCT Pub. No.: WO2018/085407
PCT Pub. Date: May 11, 2018

(65) Prior Publication Data
US 2019/0321305 A1    Oct. 24, 2019

Related U.S. Application Data

(60) Provisional application No. 62/416,574, filed on Nov. 2, 2016.

(51) Int. Cl.
| | |
|---|---|
| A61K 47/69 | (2017.01) |
| A61P 35/00 | (2006.01) |
| C07K 14/525 | (2006.01) |
| C07K 14/715 | (2006.01) |
| A61K 9/51 | (2006.01) |
| A61K 47/64 | (2017.01) |
| A61K 38/19 | (2006.01) |
| A61K 45/06 | (2006.01) |

(52) U.S. Cl.
CPC .......... *A61K 9/5153* (2013.01); *A61K 38/191* (2013.01); *A61K 45/06* (2013.01); *A61K 47/6455* (2017.08); *A61K 47/6937* (2017.08); *A61P 35/00* (2018.01); *C07K 14/525* (2013.01); *C07K 14/7151* (2013.01)

(58) Field of Classification Search
None
See application file for complete search history.

(56) References Cited

U.S. PATENT DOCUMENTS

| | | |
|---|---|---|
| 7,144,987 B1 | 12/2006 | Chirino et al. |
| 8,835,610 B2 | 9/2014 | Hsieh et al. |
| 2006/0165987 A1 | 7/2006 | Hildgen et al. |
| 2007/0207961 A1* | 9/2007 | Dahiyat ............... A61K 38/191 |
| | | 435/69.5 |
| 2008/0081075 A1 | 4/2008 | Hsiue et al. |
| 2008/0268063 A1 | 10/2008 | Jon et al. |
| 2009/0074828 A1* | 3/2009 | Alexis .................. A61K 9/5192 |
| | | 424/422 |
| 2010/0004398 A1 | 1/2010 | Wang et al. |
| 2010/0129456 A1 | 5/2010 | Ishihara et al. |
| 2011/0003007 A1 | 1/2011 | Kakizawa et al. |
| 2011/0250130 A1 | 10/2011 | Benatuil et al. |
| 2011/0251246 A1 | 10/2011 | Kufe et al. |
| 2016/0361265 A1* | 12/2016 | Fahmy ............... A61K 47/6849 |

FOREIGN PATENT DOCUMENTS

| | | |
|---|---|---|
| CN | 102000340 A | 4/2011 |
| CN | 102276813 A | 12/2011 |
| JP | 2003525612 A | 9/2003 |
| JP | 2009185261 A | 8/2009 |
| WO | WO 02/074955 A2 | 9/2002 |
| WO | 03086369 A2 | 10/2003 |
| WO | 2006014626 A2 | 2/2006 |
| WO | 2008139804 A1 | 11/2008 |
| WO | 2009051837 A2 | 4/2009 |
| WO | 2009104706 A1 | 8/2009 |
| WO | WO 2010/042866 A1 | 4/2010 |
| WO | 2012024530 A2 | 2/2012 |
| WO | WO 2012/078878 A2 | 6/2012 |
| WO | WO 2013/063114 A1 | 5/2013 |
| WO | 2013160773 A2 | 10/2013 |
| WO | WO-2013160773 A2 * | 10/2013 ........... A61K 31/454 |
| WO | 2014053882 A1 | 4/2014 |
| WO | WO 2014/053629 A1 | 4/2014 |

OTHER PUBLICATIONS

Skolnick et al (Trends Biotechnol. Jan. 2000;18(1):34-9) (Year: 2000).*
Burgess et al. (J. Cell Biol. 111:2129-2138, 1990) (Year: 1990).*
Lazar et al. (Mol. Cell. Biol., 8:1247-1252, 1988) (Year: 1988).*
Miosge (Proc Natl Acad Sci U S A. Sep. 15, 2015;112(37):E5189-98) (Year: 2015).*
Bork (Genome Research, 2000, 10:398-400) (Year: 2000).*
Laroui et al (Journal of Controlled Release 186 (2014) 41-53) (Year: 2014).*
Mann et al (Mol Pharm. Mar. 3, 2014;11(3):683-96. Epub Jan. 29, 2014) (Year: 2014).*
International Search Report and Written Opinion dated Apr. 16, 2018 in related PCT Application No. PCT/US2017/059542 filed Nov. 1, 2017 (14 pages).

(Continued)

*Primary Examiner* — Brian Gangle
*Assistant Examiner* — Andrea K McCollum
(74) *Attorney, Agent, or Firm* — Dechert LLP; Andrew T. Wilkins; Sean M. Coughlin

(57) ABSTRACT

The present invention relates to polymeric nanoparticles comprising a cytokine or a nucleic acid encoding for a cytokine, pharmaceutical compositions comprising the same, and methods for treating certain diseases comprising administering these polymeric nanoparticles to a subject in need thereof.

34 Claims, 12 Drawing Sheets

Specification includes a Sequence Listing.

(56) References Cited

OTHER PUBLICATIONS

Das et al. (2009) "Ligand-based targeted therapy for cancer tissue", Expert Opin. Drug Deliv. 6, 285-304.
Mohanty et al. (2011) "Receptor mediated tumor targeting: an emerging approach for cancer therapy", Curr. Drug Deliv. 8, 45-58.
Spriggs et al., "Recombinant Human Tumor Necrosis Factor Administered as a 24-Hour Intravenous Infusion. A Phase I and Pharmacologic Study", 1998 J Natl Cancer Inst 80 (13), pp. 1039-1044.
Sherman et al., "Recombinant Human Tumor Necrosis Factor Administered as a Five-Day Continuous Infusion in Cancer Patients: Phase I Toxicity and Effects on lipid Metabolism", 1988 Journal of Clinical Oncology February vol. 6 No. 2, pp. 344-350.
Jakob et al., "Role of Isolated Limb Perfusion With Recombinant Human Tumor Necrosis Factor a and Melphalan in Locally Advanced Extremity Soft Tissue Sarcoma", 2016 Cancer doi: 10.1002/cncr.29991.
Hallahan et al., "Spatial and temporal control of gene therapy using ionizing radiation", 1995 Nature Medicine 1 pp. 786-791.
Weichselbaum et al., "Translation of the radio-and chemo-inducible TNFerade vector to the treatment of human cancers", 2009 Cancer Gene Therapy 16, pp. 609-619; doi: 10.1038/cgt.2009.37.
Herman et al., "Randomized Phase III Multi-Institutional Study of TNFerade Biologic With Fluorouracil and Radiotherapy for Locally Advanced Pancreatic Cancer: Final Results", Mar. 1, 2013, Journal of Clinical Oncology vol. 31 No. 7, pp. 886-894.
Yin et al., "Non-viral vectors for gene-based therapy", 2014 Nature Rev. Genetics, 15, p. 541-555.
Amer M.H.,"Gene therapy for cancer: present status and future perspective", 2014 Mol Cell Ther, 2:27, p. 1-19.
Collins et al., "Gene therapy: progress and predictions", 2015 Proc. Biol. Sci. 22; 282(1821):20143003.
Kircheis et al., "Tumor-targeted gene delivery of tumor necrosis factor-a induces tumor necrosis and tumor regression without systemic toxicity", 2002 Cancer Gene Ther. 9(8), p. 673-680.
Kumar et al., "Nanotechnology in Cancer Drug Delivery and Selective Targeting", 2014 ISRN Nanotechnology vol. 2014 (2014), Article ID 939378, 12 pages.
Hasegawa et al., "Intracellular Targeting of the Oncogenic MUC1-C Protein with a novel GO-203 Nanoparticle Formulation" 2015 Clinical Cancer Research 21(10), pp. 2338.
Mann et al., Linear Short Histidine and Cysteine Modified Arginine Peptides Constitute a Potential Class of DNA Delivery Agents:, 2014 Mol. Pharmaceutics, 11(3), p. 683-696.
Pennica et al., "Human tumour necrosis factor: precursor structure, expression and homology to lymphotoxin", 1984 Nature (London), 312:724-729.
Shirai et al., "Cloning and expression in *Escherichia coli* of the gene for human tumour necrosis factor", 1985 Nature (London), 313:803.
Wang et al., "Molecular Cloning of the Complementary DNA for Human Tumor Necrosis Factor", 1985 Science, 228: 149.
Brenner et al., "Regulation of tumour necrosis factor signalling: live or let die", 2015 Nat. Rev. Immunol. Issue 15, pp. 362-374.
Gorrini et al., "Modulation of oxidative stress as an anticancer strategy", 2013 Nat Rev Drg Discov.; 12(12):931-947.
Blaser et al., "TNF and ROS Crosstalk in Inflammation", 2016 Trends Cell Biol 26(4), pp. 249-261.
Laroui Hamed et al: "Fab'-bearing siRNA TNF[alpha]-loaded nanoparticles targeted to colonic macrophages offer an effective therapy for experimental col", Journal of Controlled Release, Elsevier, Amsterdam, NL, vol. 186, May 5, 2014 (May 5, 2014), pp. 41-53, XP028855307, ISSN: 0168-3659, DOI: 10.1016/J.JCONREL.2014.04.046.
Vasundhara Shukla et al: "Systemic delivery of the tumor necrosis factor gene to tumors by a novel dual DNA-nanocomplex in a nanoparticle system", Nanomedicine: Nanotechnology, Biology and Medicine, vol. 13, No. 5, Jul. 1, 2017 (Jul. 1, 2017), pp. 1833-1839, XP055687755, NL ISSN: 1549-9634, DOI:10.1016/j.nano.2017.03.004.
Supplementary European search report of EP3534909A1 dated May 6, 2020.
Balkwell F. et al., "Smoldering and Polarized Inflammation in the Initiation and Promotion of Malignant Disease," Cancer Cell 7(3): 211-217 (2005).
Borchard et al., "The role of serum complement on the organ distribution of intravenously administered poly (methyl methacrylate) nanoparticles: effects of pre-coating with plasma and with serum complement," Pharm. Res. 7: 1055-1058 (1996).
Carswell E.A. et al., "An endotoxin-induced serum factor that causes necrosis of tumors," Proc Natl Acad Sci U.S.A., 72(9) 3666-3670 (1975).
Cho et al., 2008, "Therapeutic Nanoparticles for Drug Delivery in Cancer," Clin Cancer Res. 14: 1310-1316 (2008).
Farokhzad OC. et al., "Targeted Nanoparticle-Aptamer Bioconjugates for Cancer Chemotherapy In Vivo," Proc. Natl. Acad. Sci. U.S.A. 103(16): 6315-20 (2006).
Fonseca C, et al., "Paclitaxel-Loaded PLGA Nanoparticles: Preparation, Physicochemical Characterization and In Vitro Anti-Tumoral Activity," J. Controlled Release 83(2): 273-86 (2002).
Hanahan D. et al., "Hallmarks of Cancer: The Next Generation," Cell 144(5) 646-674 (2011).
Hood et al., "Nanocarriers for vascular delivery of antioxidants," Nanomedicine 6(7): 1257-1272 (2011).
Shi J. et al., "Engineering Biodegradable and Multifunctional Peptide-Based Polymers for Gene Delivery," J Bio Eng., 7:25; 1-10 (2013).
Sosnik et al., "Polymeric Nanocarriers: New Endeavors forthe Optimization of the Technological Aspects of Drugs," Recent Patents on Biomedical Engineering, 1: 43-59 (2008).
Spada et al., "Protein Delivery from Polymeric Nanoparticles," World Academy of Science, Engineering and Technology 5(4); 172-176 (2011).
Sundar et al., "Biopolymeric Nanoparticles" Sci Technol of Adv Mater. doi:10.1088/1468-6996/11/1/014104 (2010).
Topalian S. et al., "Immune Checkpoint Blockade: A Common Denominator Approach to Cancer Therapy," Cancer Cell, 27(4); 450-461 (2015).
Xu R. et al., "An Injectable Nanoparticle Generator Enhances Delivery of Cancer Therapeutics," Nat Biotechnol. 34(4): 414-418 (2016).
Essa et al., "Charaterization of rhodamine loaded PEG-g-PLA nanoparticles (NPs): Effect of poly(ethylene glycol) grafting density.", International Journal of Pharmaceuticals., 2011, vol. 411, pp. 178-187.
Essa et al., "Effect of polyethylene glycol (PEG) chain organization on the physicochemical properties of poly(D,L-Tactide) (PLA) based nanoparticles", European Journal of Pharmaceutics and Biopharmaceutics, 2010, vol. 75, pp. 96-106.
Farokhzad et al. "Nanoparticle-Aptamer Bioconjugates: A New Approach for Targeting Prostate Cancer Cells", Cancer Research, Nov. 1, 2014, vol. 64, pp. 7668-7672.
HiMedia Laboratories, "Pluronic® F-68", Product Information (http://himedialabs.com/TD/TC222.pdf, accessed Aug. 30, 2020).
Hyuk Sang Yoo et al., "Biodegradable Nanoparticles Containing Doxorubicin-PLGA Conjugate for Sustained Release", Pharmaceutical Research, Jan. 1, 1999, vol. 16, No. 7, pp. 1114-1118, XP008128802.
International Preliminary Report on Patentability from PCT/IB2013/001247 dated Oct. 28, 2014.
International Search Report from PCT/IB2013/001247 dated Jan. 21, 2014.
Jain et al., "PEG-PLA-PEG block copolymeric nanoparticles for oral immunization against hepatitis B.", International Journal of Pharmaceuticals., 2010, vol. 287, pp. 253-262.
Kimetal, Preparation and characterization of biodegradable nanospheres composed of methoxy poly(ethylene glycol) and DL-lactide block copolymer as novel drug carriers, Journal of Controlled Release, 1998, vol. 56, 197-208.
Kim et al., "Nanoparticle delivery of a peptide targeting EGFR signaling", Journal of Controlled Release, vol. 157, Issue 2, Jan. 30, 2012, pp. 279-286.
Kim et al., Poly(ethylene oxide)-poly(propylene oxide)-poly(ethylene oxide)/poly(?-caprolactone)(PCL) amphiphilic block copolymeric nanospheres IL Thermo-responsive drug release behaviors, Journal of Controlled Release, Apr. 3, 2000, vol. 65, 345-358.

(56) References Cited

OTHER PUBLICATIONS

Kunii et al., "Preparation and antitumor characteristics of PLA/(PEG-PPG-PEG) nanoparticles loaded with camptothecin,", European Journal of Pharmaceutics and Biopharmaceutics, vol. 67, No. 1, Aug. 2007, pp. 9-17.

Mosquiera, Interactions between a Macrophage Cell Line (J774A1) and Surface-modified Poly(D,L-lactide) Nanocapsules Bearing Poly-(ethylene glycol), Journal of Drug Targeting, 1999, vol. 7, No. 1, pp. 65-78.

Onishi, "Antitumor Properties of Irinotecan-Containing Nanoparticles Prepared Using Poly(DL-lactic acid) and Poly (ethylene glycol)-block-poly(propylene glycol)-block-poly(ethylene glycol).", Biol. Pharm. Bull., 2003, vol. 26, No. 1, pp. 116-119.

Wang et al., "Novel PEG-graft-PLA nanoparticles with the potential for encapsulation and controlled release of hydrophobic and hydrophilic medications in aqueous medium", International Journla of Nanomedicine, 2011, vol. 6, pp. 1443-1451, doi: 10.2147/IJN.S19765. Epub Jul. 7, 2011.

Xiong et al., "Synthesis and Aggregation Behavior of Pluronic F127/Poly(lactic acid) Block Copolymers in Aqueous Solution," 2003, American Chemical Society, Macromolecules, vol. 36, No. 26, pp. 9979-9985.

Yoo Hyuk Sang et al., "Biodegradable polymeric micelles composed of doxorubicin conjugated PLGA-PEG block copolymer", Journal of Controlled Release, Jan. 29, 2001, vol. 70, No. 1-2, pp. 63-70, XP002473697.

Perego et al., "Effect of Molecular Weight and Crystallinity on Poly(lactic acid) Mechanical Properties," J Appl Polym Sci., 1996:59:3743.

Ten Hagen et al., "Pegylated liposomal tumor necrosis factor-alpha results in reduced toxicity and synergistic antitumor activity after systemic administration in combination with liposomal doxorubicin (Doxil) in soft tissue sarcoma-bearing rats." Int J Cancer. 2002;97(1):115-20.

Pastorakova et al., "Tumor targeted gene therapy with plasmid expressing human tumor necrosis factor alpha in vitro and in vivo." Neoplasma. 2005;52(4):344-51.

\* cited by examiner

| Samples | Particle Size (nm) | PDI |
|---|---|---|
| NC | 80 ± 4 | 0.08 |
| NP | 170 ± 2 | 0.21 |
| PD NPs | 190 ± 5 | 0.43 |
| PPDNPs | 250 ± 7 | 0.11 |

NC: Peptide-TNF DNA Nanocomplexes
NP: PLA-PEG nanoparticles (NPs)
PDNPs: TNF-DNA-encapsulated NPs
PPDNPs: peptide-TNF DNA nanocomplexes –encapsulated in PLA-PEG NPs NC: Peptide-TNF DNA Nanocomplexes
NP: PLA-PEG nanoparticles (NPs)
PD: TNF-DNA-encapsulated NPs
PPD: peptide-TNF DNA nanocomplexes –encapsulated in PLA-PEG NPs FIGURE 3A
FIGURE 3B
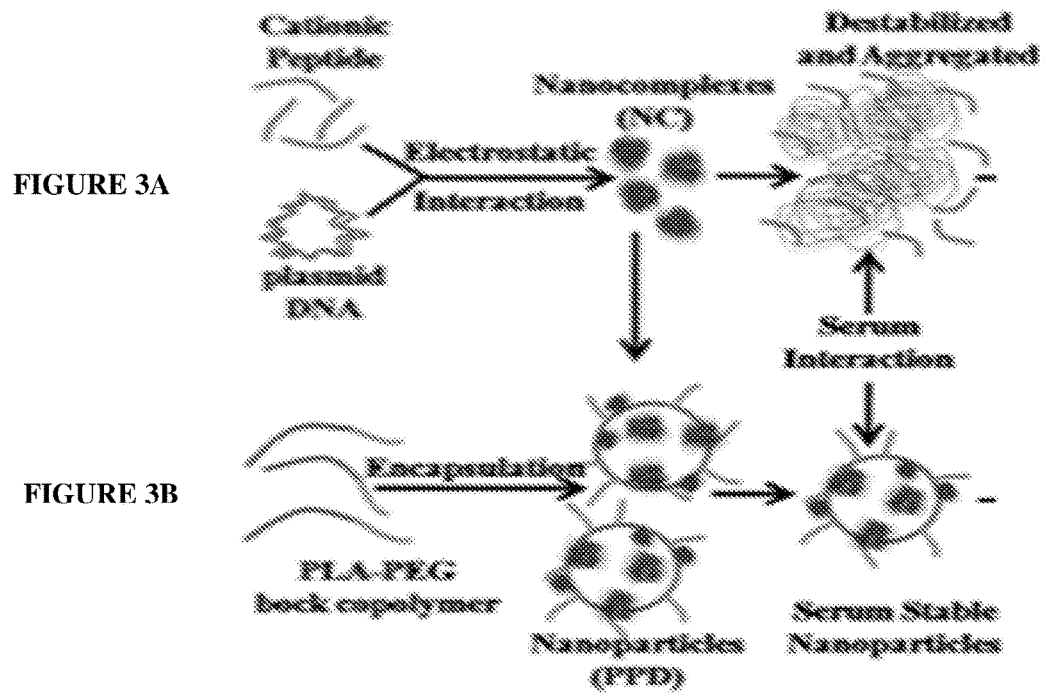
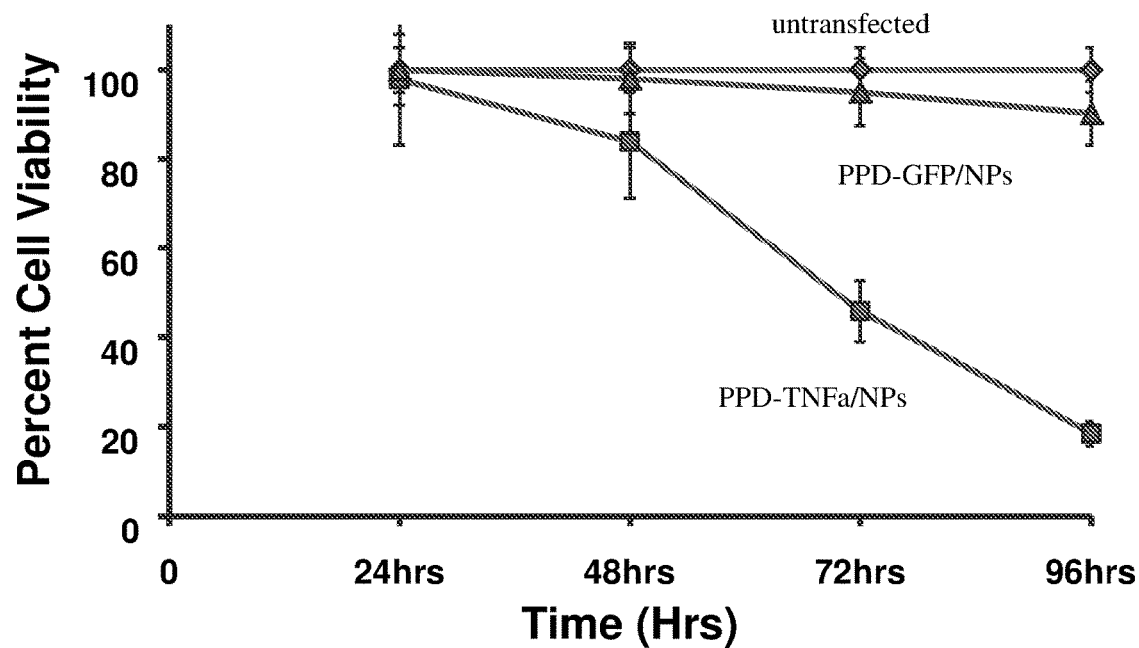
FIGURE 3C

SEQUENCE LISTING

<160> NUMBER OF SEQ ID NOS: 11

<210> SEQ ID NO 1
<211> LENGTH: 16
<212> TYPE: PRT
<213> ORGANISM: Homo sapiens

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 18
<212> TYPE: PRT
<213> ORGANISM: Homo sapiens

<400> SEQUENCE: 2

Leu Leu Ile Ile Leu Arg Arg Arg Ile Arg Lys Gln Ala His Ala His
1               5                   10                  15

Ser Lys

```
<210> SEQ ID NO 3
<211> LENGTH: 27
<212> TYPE: PRT
<213> ORGANISM: Homo sapiens

<400> SEQUENCE: 3

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 4
<211> LENGTH: 27
<212> TYPE: PRT
<213> ORGANISM: Homo sapiens

<400> SEQUENCE: 4

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 5
<211> LENGTH: 21
<212> TYPE: PRT
<213> ORGANISM: Homo sapiens

<400> SEQUENCE: 5

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 6
<211> LENGTH: 18
<212> TYPE: PRT
<213> ORGANISM: Homo sapiens

<400> SEQUENCE: 6

Lys Leu Ala Leu Lys Leu Ala Leu Lys Ala Leu Lys Ala Ala Leu Lys
1               5                   10                  15

Leu Ala

<210> SEQ ID NO 7
<211> LENGTH: 9
<212> TYPE: PRT
<213> ORGANISM: Homo sapiens

<400> SEQUENCE: 7

Arg Arg Trp Trp Arg Arg Trp Arg Arg
1               5

<210> SEQ ID NO 8
<211> LENGTH: 18
<212> TYPE: PRT
<213> ORGANISM: Homo sapiens

<400> SEQUENCE: 8

Cys Arg Arg Arg Arg Arg His His His His His His Arg Arg Arg
1               5                   10                  15

Arg Cys
```

-continued

<210> SEQ ID NO 9
<211> LENGTH: 157
<212> TYPE: PRT
<213> ORGANISM: Homo sapiens

<400> SEQUENCE: 9

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Asp Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 10
<211> LENGTH: 233
<212> TYPE: PRT
<213> ORGANISM: Homo sapiens

<400> SEQUENCE: 10

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

```
Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 11
<211> LENGTH: 1686
<212> TYPE: DNA
<213> ORGANISM: Homo sapiens

<400> SEQUENCE: 11

| | | | | | |
|---|---|---|---|---|---|
| cagacgctcc | ctcagcaagg | acagcagagg | accagctaag | agggagagaa | gcaactacag | 60 |
| accccccctg | aaaacaaccc | tcagacgcca | catcccctga | caagctgcca | ggcaggttct | 120 |
| cttcctctca | catactgacc | cacggctcca | ccctctctcc | cctggaaagg | acaccatgag | 180 |
| cactgaaagc | atgatccggg | acgtggagct | ggccgaggag | gcgctcccca | agaagacagg | 240 |
| ggggcccag | ggctccaggc | ggtgcttgtt | cctcagcctc | ttctccttcc | tgatcgtggc | 300 |
| aggcgccacc | acgctcttct | gcctgctgca | ctttggagtg | atcggccccc | agagggaaga | 360 |
| gttcccagg | gacctctctc | taatcagccc | tctggcccag | gcagtcagat | catcttctcg | 420 |
| aaccccgagt | gacaagcctg | tagcccatgt | tgtagcaaac | cctcaagctg | aggggcagct | 480 |
| ccagtggctg | aaccgccggg | ccaatgccct | cctggccaat | ggcgtggagc | tgagagataa | 540 |
| ccagctggtg | gtgccatcag | agggcctgta | cctcatctac | tcccaggtcc | tcttcaaggg | 600 |
| ccaaggctgc | ccctccaccc | atgtgctcct | cacccacacc | atcagccgca | tcgccgtctc | 660 |
| ctaccagacc | aaggtcaacc | tcctctctgc | catcaagagc | ccctgccaga | gggagacccc | 720 |
| agagggggct | gaggccaagc | cctggtatga | gcccatctat | ctgggagggg | tcttccagct | 780 |
| ggagaagggt | gaccgactca | gcgctgagat | caatcggccc | gactatctcg | actttgccga | 840 |
| gtctgggcag | gtctactttg | gatcattgc | cctgtgagga | ggacgaacat | ccaaccttcc | 900 |
| caaacgcctc | ccctgcccca | atcccttat | taccccctcc | ttcagacacc | ctcaacctct | 960 |
| tctggctcaa | aaagagaatt | gggggcttag | ggtcggaacc | caagcttaga | actttaagca | 1020 |
| acaagaccac | cacttcgaaa | cctgggattc | aggaatgtgt | ggcctgcaca | gtgaagtgct | 1080 |
| ggcaaccact | aagaattcaa | actggggcct | ccagaactca | ctggggccta | cagctttgat | 1140 |
| ccctgacatc | tggaatctgg | agaccaggga | gcctttggtt | ctggccagaa | tgctgcagga | 1200 |
| cttgagaaga | cctcacctag | aaattgacac | aagtggacct | taggccttcc | tctctccaga | 1260 |
| tgtttccaga | cttccttgag | acacggagcc | cagccctccc | catggagcca | gctccctcta | 1320 |
| tttatgtttg | cacttgtgat | tatttattat | ttatttatta | tttatttatt | tacagatgaa | 1380 |
| tgtatttatt | tgggagaccg | gggtatcctg | ggggacccaa | tgtaggagct | gccttggctc | 1440 |
| agacatgttt | tccgtgaaaa | cggagctgaa | caataggctg | ttcccatgta | gccccctggc | 1500 |
| ctctgtgcct | tcttttgatt | atgttttta | aaatatttat | ctgattaagt | tgtctaaaca | 1560 |
| atgctgattt | ggtgaccaac | tgtcactcat | tgctgagcct | ctgctcccca | ggggagttgt | 1620 |
| gtctgtaatc | gccctactat | tcagtggcga | gaaataaagt | ttgcttagaa | aagaaaaaaa | 1680 |
| aaaaaa | | | | | | 1686 |

POLYMERIC NANOPARTICLES PROVIDING NUCLEIC ACIDS ENCODING TNF-α

RELATED APPLICATIONS

This application is a 35 U.S.C. § 371 filing of International Patent Application No. PCT/US2017/059542, filed Nov. 1, 2017, which claims the benefit of priority of U.S. Provisional Patent Application No. 62/416,574, filed Nov. 2, 2016, the contents of which are incorporated by reference in their entirety.

FIELD

The present invention relates to the field of nanotechnology, in particular, to the use of biodegradable polymeric nanoparticles for the delivery of therapeutic agents.

BACKGROUND

Cancer is one of the most devastating diseases and it involves various genetic alterations and cellular abnormalities. This complexity and heterogeneity promotes the aggressive growth of cancer cells leading to significant morbidity and mortality in patients (Das, M. et al. (2009) Ligand-based targeted therapy for cancer tissue. Expert Opin. Drug Deliv. 6, 285-304; Mohanty, C. et al. (2011) Receptor mediated tumor targeting: an emerging approach for cancer therapy. Curr. Drug Deliv. 8, 45-58).

Immunotherapeutic approaches, particularly PD-1/PD-L1 blockade, have improved the treatment of certain human cancers, supporting the premise that evasion of immune destruction is of importance for cancer progression. However, many cancers fail to respond to immunotherapy, at least in part, by suppression of a proinflammatory tumor microenvironment.

A hallmark of diverse cancers is the capacity to circumvent immune destruction (Hanahan D. et al., 2011 Cell Volume 144, Issue 5 pages 646-674). Indeed, cancers are often infiltrated with immune cells that are ineffective in the recognition of tumor antigens and are in turn exploited to promote a pro-tumorigenic microenvironment (Balkwell F. et al. 2005 Cancer Cell 7(3), pages 211-217). Interestingly, however, the presence of immune cell infiltrates in what are referred to as "hot" tumors is associated with improved responsiveness to cytotoxic agents, anti-tumor vaccines and immune checkpoint inhibitors (Topalian S. et al., 2015 Cancer Cell, (4), pages 450-461). These findings have emphasized the potential importance of reprogramming the microenvironment of "hot" and "cold" tumors with immune infiltrates that are effective in recognizing and destroying cancer cells.

TNF was discovered as an endotoxin-inducible factor that induced necrosis of tumors (Carswell E. A. et al., PNAS, 1975 Proc. Nat. Acad. Sci. Vol. 72, No. 9, pages 3666-3670). Since then, TNF has been one of the most extensively studied cytokines, based in part on the findings that it regulates pro-inflammatory responses, cell differentiation and cell death (Brenner D. et al., 2015 Nat. Rev. Immunol. Issue 15, pages 362-374). In addition, the effectiveness of recombinant human TNF as an anti-cancer agent has been investigated, however some investigators have found systemic side effects, such as fever, fatigue and hypotension, precluded for some its further development (Spriggs D. R. et al., 1988 J Natl Cancer Inst 80(13), pages 1039-1044.; Sherman M. L. et al., 1988 JCO February vol. 6 no. 2, pages 344-350).

As a way of ameliorating the systemic toxicities, TNF has been approved in Europe for administration by isolated limb perfusion in the treatment of patients with locally advanced extremity soft tissue sarcoma (Jakob J. et al., 2016 Cancer doi: 10.1002/cncr.29991). Another attempted approach for the clinical development of TNF involved intratumoral delivery of an adenoviral vector encoding TNF under the control of a radio- and chemo-inducible promoter (TNFerade) (Hallahan D. et al., 1995 Nature Medicine 1 pages 786-791). In early phase trials of TNFerade in combination with radiotherapy, significant clinical activity was observed in patients with metastatic melanoma, soft tissue sarcoma and locally advanced esophageal cancer (Weichselbaum R. et al., 2009 Cancer Gene Therapy 16, pages 609-619; doi:10.1038/cgt.2009.37). Anti-tumor activity was also observed in patients with pancreatic, rectal, and head and neck cancers (Ibid.). However, a phase III trial of TNFerade in patients with locally advanced pancreatic cancer failed to demonstrate a survival benefit (Herman J. M. et al., 2013 JCO vol. 31 no. 7, pages 886-894), prompting the sponsor to discontinue the development of this agent.

TNF is an effective agent for the treatment of human cancers; however additional approaches need to be developed to utilize the anti-tumor activity of TNF in a manner that limits systemic side effects.

SUMMARY

An aspect of the invention provides a composition comprising: polymeric nanoparticles comprising a block copolymer comprising poly(lactic acid) (PLA) and poly(ethylene glycol) (PEG); and a TNF-α protein comprising the amino acid sequence of SEQ ID NO: 9, or a portion thereof. In various embodiments, the TNF-α protein comprises an amino acid sequence that is at least 70%-99% identical to the sequence of SEQ ID NO: 9, or a portion thereof. In various embodiments, the TNF-α protein comprises an amino acid sequence of SEQ ID NO: 10 or that is at least 50%-99% (for example at last 70%) identical to the sequence of SEQ ID NO: 10, or a portion thereof.

An aspect of the invention provides a composition comprising: polymeric nanoparticles comprising a block copolymer comprising PLA and PEG; and an isolated nucleic acid comprising the sequence of SEQ ID NO: 11, or a portion thereof. In various embodiments, the isolated nucleic acid comprises an amino acid sequence that is at least 70-99% identical to the sequence of SEQ ID NO: 11, or a portion thereof. For example, the isolated nucleic sequence encodes the sequence of SEQ ID NO: 9 or SEQ ID NO: 10.

In various embodiments of the composition, the polymeric nanoparticle comprises poly(lactic acid)-poly(ethylene glycol) (PLA-PEG) di-block copolymer.

In various embodiments of the composition, the polymeric nanoparticle comprises poly(lactic acid)-poly(ethylene glycol)-poly(propylene glycol)-poly(ethylene glycol) (PLA-PEG-PPG-PEG) tetra-block copolymer.

In various embodiments of the composition, the PLA-PEG-PPG-PEG tetra-block copolymer is formed from conjugation of PEG-PPG-PEG tri-block copolymer with PLA. For example, the conjugation is a chemical conjugation.

In various embodiments of the composition, the molecular weight of PLA is between about 10,000 and about 100,000 daltons. For example, the molecular weight of the PLA is about 10,000; 20,000; 30,000; 40,000; 50,000; 60,000; 70,000; 80,000; 90,000, or 100,000 daltons. In a further embodiment, the molecular weight of the PLA is about 12,000 daltons (i.e., 12 kDA) or about 72,000 daltons (i.e., 72 kDA).

In various embodiments of the composition, the TNF-α protein, or a portion thereof, comprises an amino acid sequence at least 70%, 75%, 80%, 85%, 90%, 95%, or 99% identical to SEQ ID NO: 9 or a portion thereof. In various embodiments, the TNF-α protein, or a portion thereof, comprises an amino acid sequence at least 70%, 75%, 80%, 85%, 90%, 95%, or 99% identical to SEQ ID NO: 10 or a portion thereof.

In various embodiments of the composition, the isolated nucleic acid comprises the sequence of SEQ ID NO: 11 or a portion thereof. In various embodiments of the composition, the isolated nucleic acid encodes the TNF-α protein, or a portion thereof, that comprises an amino acid sequence at least 70%, 75%, 80%, 85%, 90%, 95%, or 99% identical to SEQ ID NO: 9 or a portion thereof. In various embodiments of the composition, the isolated nucleic acid encodes the TNF-α protein, or a portion thereof, that comprises an amino acid sequence at least 70%, 75%, 80%, 85%, 90%, 95%, or 99% identical to SEQ ID NO: 10 or a portion thereof.

In various embodiments, the composition further comprises a cationic peptide. In various embodiments, the composition further comprises a cell-penetrating peptide. In various embodiments, the composition further comprises a cationic cell-penetrating peptide. In various embodiments, the peptide comprises an amino acid sequence selected from the group consisting of SEQ ID NOs: 1, 2, 3, 4, 5, 6, 7, 8, and polyarginine. For example, the polyarginine comprises at least about 2-20 arginines. In various embodiments, the polyarginine comprises at least about 2, 5, 7 or 9 arginines.

In various embodiments, the composition further comprises a C-cyclized poly-cationic peptide. For example, the C-cyclized poly-cationic peptide comprises the amino acid sequence of SEQ ID NO: 8 or a portion thereof.

In various embodiments of the composition, the cell-penetrating or cationic peptide and the isolated nucleic acid form a complex.

In various embodiments, the composition further comprises a chemotherapeutic agent or a targeted anti-cancer agent selected from the group consisting of doxorubicin, daunorubicin, decitabine, irinotecan, SN-38, cytarabine, docetaxel, triptolide, geldanamycin, 17-AAG, 5-FU, oxaliplatin, carboplatin, methotrexate, paclitaxel, indenoisoquinolines, bortezomib, and combinations thereof.

An aspect of the invention provides a pharmaceutical composition comprising: polymeric nanoparticles comprising a block copolymer comprising poly(lactic acid) (PLA) and poly(ethylene glycol) (PEG); and a TNF-α protein comprising the amino acid sequence at least 70% identical to the sequence of SEQ ID NO: 9, or a portion thereof, or an isolated nucleic acid comprising the sequence of SEQ ID NO: 11 or encodes a TNF-α protein comprising the amino acid sequence at least 70% identical to the sequence of SEQ ID NO: 9 or 10, or a portion thereof, for use in treating a disease selected from the group consisting of cancer, an autoimmune disease, an inflammatory disease, a metabolic disorder, a developmental disorder, a cardiovascular disease, liver disease, an intestinal disease, an infectious disease, an endocrine disease and a neurological disorder.

In various embodiments of the composition, the polymeric nanoparticles are formed of a polymer consisting essentially of poly(lactic acid)-poly(ethylene glycol) (PLA-PEG) di-block copolymer.

In various embodiments of the composition, the polymeric nanoparticles are formed of a polymer consisting essentially of poly(lactic acid)-poly(ethylene glycol)-poly(propylene glycol)-poly(ethylene glycol) (PLA-PEG-PPG-PEG) tetra-block copolymer. In various embodiments, the polymeric nanoparticle comprises the tetra-block copolymer described in Table 5.

In various embodiments of the composition, the polymeric nanoparticles further comprise a targeting moiety attached to the outside of the polymeric nanoparticles, and wherein the targeting moiety is an antibody, peptide, or aptamer. In various embodiments the targeting moiety comprises an immunoglobulin molecule, an scFv, a monoclonal antibody, a humanized antibody, a chimeric antibody, a humanized antibody, a Fab fragment, an Fab' fragment, an F(ab')2, an Fv, and a disulfide linked Fv.

An aspect of the invention provides a polymeric nanoparticle formed of a polymer consisting essentially of a PLA-PEG-PPG-PEG tetra-block copolymer or PLA-PEG di-block copolymer, wherein the polymeric nanoparticles are loaded with a cytokine, or a portion thereof, or an isolated nucleic acid that encodes for the cytokine, or a portion thereof.

In various embodiments of the invention, the cytokine is at least 70% identical to the sequence of SEQ ID NO: 9 or a portion thereof. In various embodiments of the invention, the cytokine is at least 70% identical to the sequence of SEQ ID NO: 10 or a portion thereof. In various embodiments of the method, the amino acid sequence is at least 80%, at least 85%, at least 90%, at least 95%, at least 98% or at least 99% identical to the amino acid sequence of SEQ ID NO: 9 or SEQ ID NO: 10.

In various embodiments, the isolated nucleic acid is complexed with a cationic cell-penetrating peptide. For example, the cationic cell-penetrating peptide is selected from the group consisting of SEQ ID NOs: 1, 2, 3, 4, 5, 6, 7, 8, and polyarginine.

An aspect of the invention provides a method for treating cancer in a subject in need thereof comprising administering to the subject a therapeutically effective amount of a pharmaceutical composition comprising
a) a polymeric nanoparticle formed of a polymer comprising PLA-PEG di-block copolymer; and
b) a TNF-α protein comprising the amino acid sequence at least 70% identical to the sequence of SEQ ID NO: 9, or a portion thereof, or an isolated nucleic acid that encodes a TNF-α protein comprising the amino acid sequence at least 70% identical to the sequence of SEQ ID NO: 9, or a portion thereof. For example, the isolated nucleic acid comprises the nucleic acid sequence of SEQ ID NO: 11.

In various embodiments of the method, the pharmaceutical composition further comprises a chemotherapeutic agent or a targeted anti-cancer agent selected from the group consisting of doxorubicin, daunorubicin, decitabine, irinotecan, SN-38, cytarabine, docetaxel, triptolide, geldanamycin, 17-AAG, 5-FU, oxaliplatin, carboplatin, methotrexate, paclitaxel, indenoisoquinolines, bortezomib, and combinations thereof.

In various embodiments of the method, the cancer is breast cancer, prostate cancer, non-small cell lung cancer, metastatic colon cancer, pancreatic cancer, or a hematological malignancy. For example, the cancer comprises a PD-1 refractory tumor.

In various embodiments of the method, the amino acid sequence is at least 80%, at least 85%, at least 90%, at least 95%, at least 98% or at least 99% identical to the amino acid sequence of SEQ ID NO: 9.

An aspect of the invention provides a method for inducing TNF expression in a cell, comprising contacting the cell with an effective amount of polymeric nanoparticles formed of a polymer comprising PLA-PEG di-block copolymer; wherein the polymeric nanoparticles comprise an isolated nucleic acid that encodes a TNF-α protein comprising the amino acid sequence at least 70% identical to the sequence of SEQ ID NO: 9, or a portion thereof. For example, the isolated nucleic acid comprises the nucleic acid sequence of SEQ ID NO: 11.

In various embodiments of the method, the TNF-α protein, or a portion thereof, comprises an amino acid sequence at least 70%, 75%, 80%, 85%, 90%, 95%, or 99% identical to SEQ ID NO: 9.

In various embodiments of the method, the isolated nucleic acid encodes the TNF-α protein, or a portion thereof, that comprises an amino acid sequence at least 70%, 75%, 80%, 85%, 90%, 95%, or 99% identical to SEQ ID NO: 9.

In various embodiments of the method, the isolated nucleic acid is complexed with a cationic cell-penetrating peptide. For example, the cationic cell-penetrating peptide is selected from the group consisting of SEQ ID NOs: 1, 2, 3, 4, 5, 6, 7, 8 and polyarginine.

In various embodiments of the method, the nanoparticles are formed of a polymer consisting essentially of PLA-PEG di-block copolymer.

In various embodiments of the method, the nanoparticles are formed of a polymer consisting essentially of PLA-PEG-PPG-PEG tetra-block copolymer. In various embodiments of the method, the polymeric nanoparticle comprises a tetra-block copolymer found in Table 5.

In various embodiments of the methods provided herein, the molecular weight of PLA is between about 10,000 and about 100,000 daltons. For example, the molecular weight of the PLA is about 10,000; 20,000; 30,000; 40,000; 50,000; 60,000; 70,000; 80,000; 90,000, or 100,000 daltons. In a further embodiment, the molecular weight of the PLA is about 12,000 daltons (i.e., 12 kDA) or about 72,000 daltons (i.e., 72 kDA).

In various embodiments of any of the compositions or methods provided herein, the nanoparticle is formed of the block copolymer comprising poly(lactic acid) (PLA) and poly(ethylene glycol) (PEG); and the TNF-α protein, or the isolated nucleic acid encoding TNF-α protein. In an embodiment, the nanoparticle releases the protein or the isolated nucleic acid over a period of time. In a further embodiment, the period of time is at least 1 day to 20 days. In various embodiments of the method, the period of time is about 5 days to 10 days.

BRIEF DESCRIPTION OF THE FIGURES

The following figures form part of the present specification and are included to further illustrate aspects of the present invention.

FIGS. 1 (A, B, C, and D) are a set of photomicrographs and graphs characterizing nanocomplexes and nanoparticles described herein.

FIGS. 2 (A, B, and C) show the efficacy and toxicity of NC-GFP and PPD-GFP NP's over time.

FIGS. 3 (A, B, and C) show the generation, expression and functional effect of antitumor protein encoding plasmid DNA (pE425-TNFα) in MDA-MB-231 cells.

FIG. 3A is a drawing showing plasmid DNA and cationic peptides electrostatically interacting to form nanocomplexes. The resulting nanocomplexes become destabilized and aggregated once interacting with serum.

FIG. 3B is a drawing showing nanoparticle encapsulation of the complexes of FIG. 3A with PLA-PEG block copolymers to form serum stable cationic peptide-plasmid DNA nanoparticles.

FIG. 3C is a graph showing percent cell viability (ordinate) after 24, 48, 72 and 96 hours of PPD-GFP/NPs or PPD-TNF-α treatment. Control cells were untransfected.

FIGS. 4 (A, B, and C) show expression and functional effect of antitumor protein encoding plasmid DNA (pE425-TNFα) in MCF-7 cells.

FIGS. 6 (A and B) show in vivo tumor regression efficacy after treatment of plasmid DNA (pDNA-TNFα), peptide-pDNA nanocomplexes (NC-TNFα) and PLA-PEG-peptide-pDNA nanoparticles (PPD-TNFα) on EAT bearing syngeneic BALB/c mice. Tumor bearing mice were administered intraperitoneally with saline (Ctrl), pDNA-TNFα_1.2 mg/kg, NC-TNFα_1.2 mg/kg, PPD-TNFα_0.6 mg/kg, PPD-TNFα_1.2 mg/kg on days 1, 5, 9, 13, 17, 21 with initial tumor volume as 50 mm³. Each data point represents the mean tumor size ±SEM (n=6).

Figure 6A:
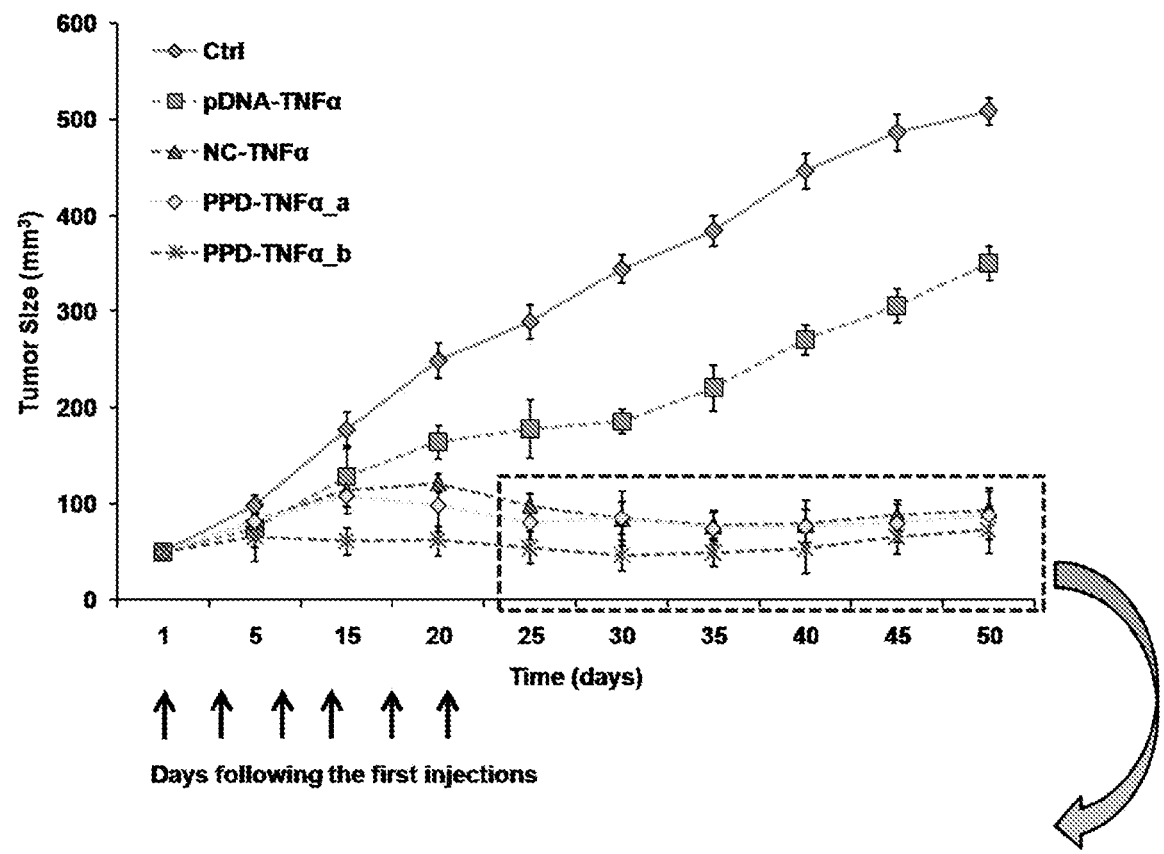

FIG. 6A is a graph showing tumor size (ordinate) over time (abscissa) for BALB-C mice intraperitoneally administered the different nanoparticles: peptide-pDNA nanocomplexes (NC-TNFα); pDNA-TNFα-pDNA-TNFα_1.2 mg/kg; PPD-TNFα_a-PPD-TNFα_0.6 mg/kg (IP); and PPD-TNFα_b-PPD-TNFα_1.2 mg/kg(IP)

Figure 6B:
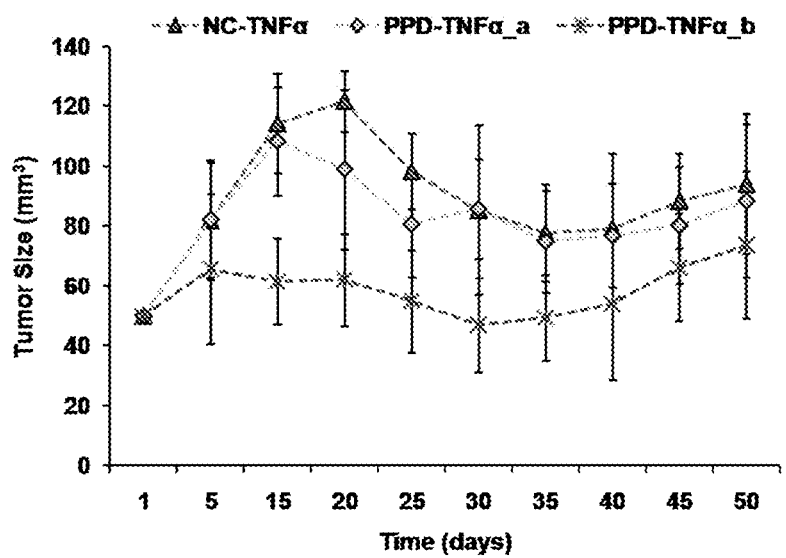

FIG. 6B shows is an expanded view graph showing tumor size (ordinate) over time for the BALB-C mice of FIG. 6A that were intraperitoneally administered different nanoparticles.

FIGS. 7 (A and B) show tumor size and tumor volumes for BALB-C mice intratumorally administered a plasmid DNA (pDNA-TNFα), peptide-pDNA nanocomplexes (NC-TNFα) and PLA-PEG-peptide-pDNA nanoparticles (PPD-TNFα) on EAT bearing syngeneic BALB/c mice. Tumor bearing mice were administered intraperitoneally with saline (Ctrl), pDNA-TNFα 1.2 mg/kg, NC-TNFα 1.2 mg/kg, PPD-TNFα 0.6 mg/kg, PPD-TNFα 1.2 mg/kg on days 1, 5, 9, 13, 17, 21 with initial tumor volume as 50 mm³. Each data point represents the mean tumor size ±SEM (n=6).

Figure 7A:
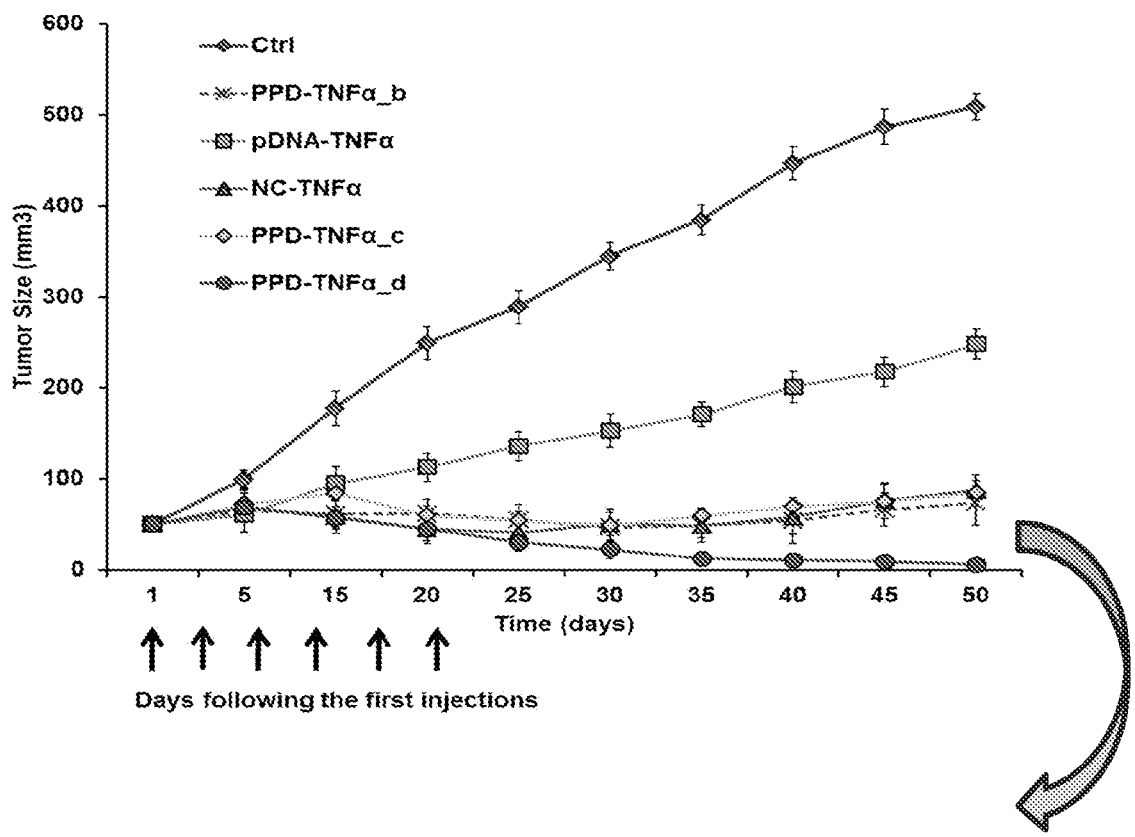

FIG. 7A is a graph showing tumor size (ordinate) over time (abscissa) for BALB-C mice intratumorally administered different nanoparticles.

Figure 7B:
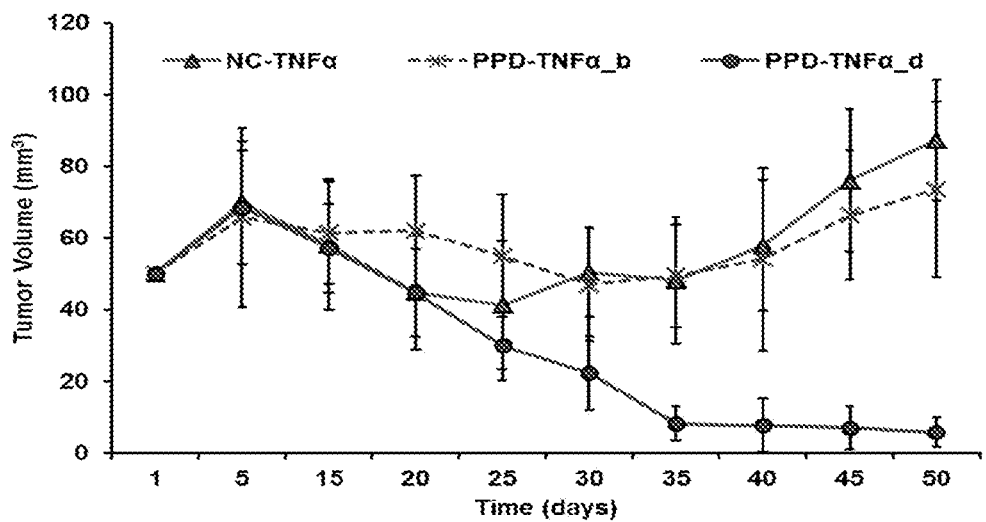

FIG. 7B shows is a graph tumor volume (ordinate) over time for time for the BALB-C mice of FIG. 7A that were intratumorally administered different nanoparticles.

Figure 8:
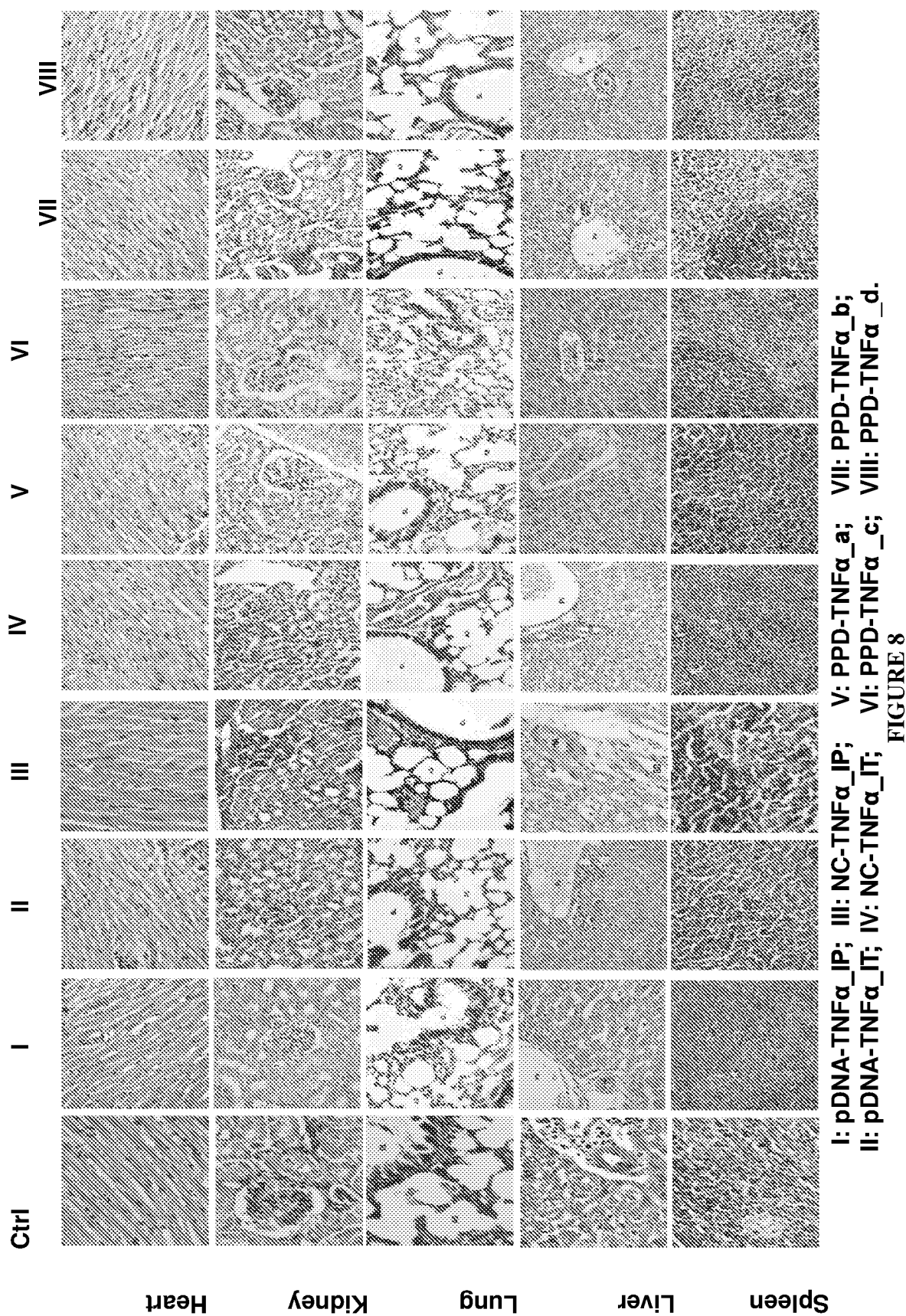

FIG. 8 is a set of photomicrographs of hematoxylin and eosin tumor tissues from murine subjects intraperitoneally or intratumorally administered plasmids, nanocomplexes or nanoparticles described herein.

Figure 9A:
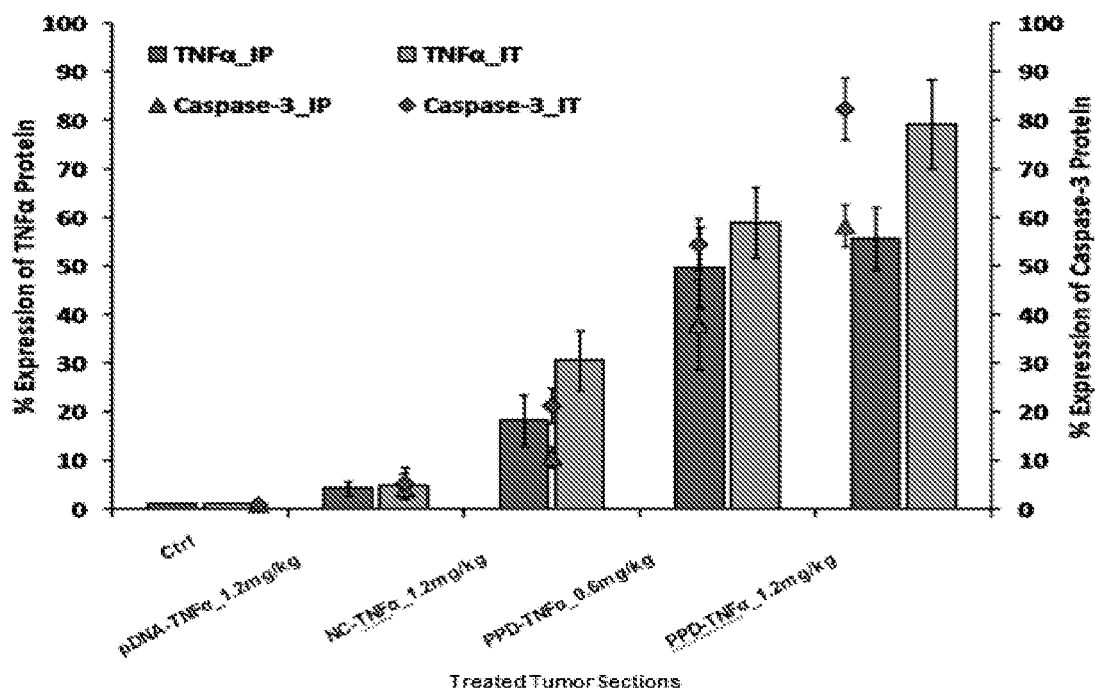

FIG. 9A is a graph showing fluorescence-activated cell sorting (FACS) analysis of TNFα and caspase-3 protein in excised tumor tissues treated with pDNA-TNFα 1.2 mg/kg, NC-TNFα 1.2 mg/kg, PPD-TNFα 0.6 mg/kg, PPD-TNFα 1.2 mg/kg a third day of the last IP injection or the IT injection.

Figure 9B:
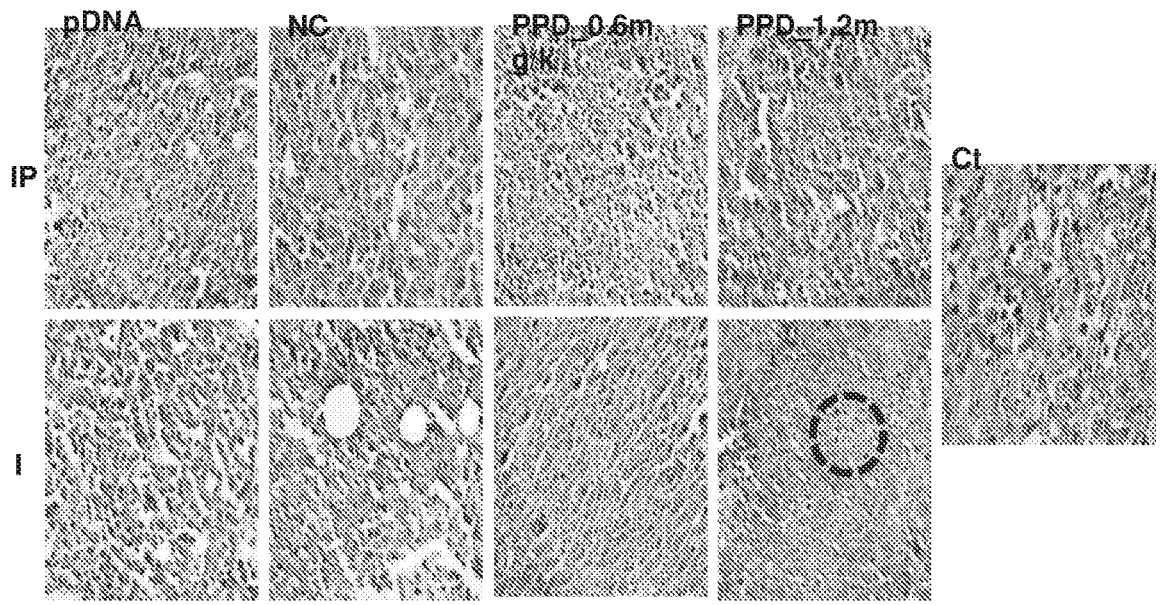

FIG. 9B is a set of high power photomicrographs of hematoxylin and eosin (H&E) stained tumor tissues treated with pDNA-TNFα 1.2 mg/kg, NC-TNFα 1.2 mg/kg, PPD-TNFα 0.6 mg/kg and PPD-TNFα 1.2 mg/kg. Fragmented nuclei along with several apoptotic bodies were seen in the tumor treated with PPD-TNFα 1.2 mg/kg by IT injections indicated by dotted circle (fourth column from the left bottom row) as compared to intact nuclei in ctrl indicated by dotted circle (fifth column from the left).

Figure 10:
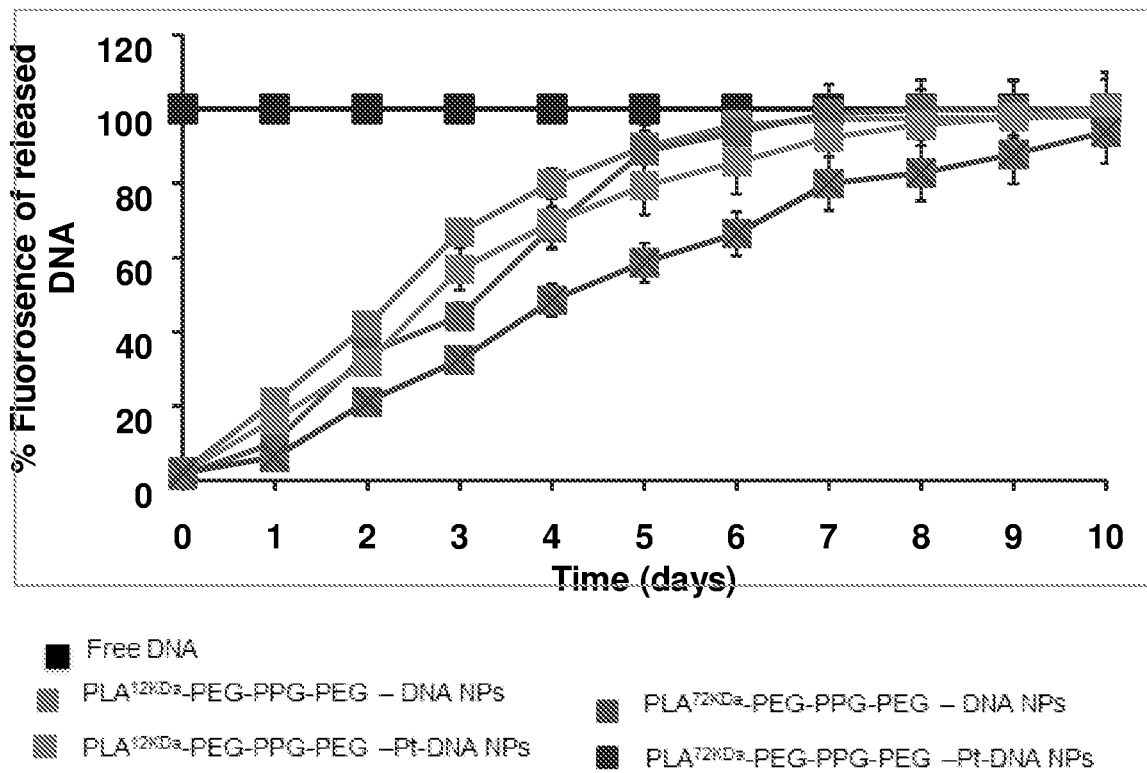

FIG. 10 is a line graph showing a comparison of TNF DNA release profiles in non-physiological buffer (PBS ph 7.4). Percent fluorescence of released DNA (ordinate) is shown as a function of time (days; abscissa) for free DNA only; PLA 12 KDa-PEG-PPG-PEG TNF-DNA nanoparticles; PLA 12 KDa-PEG-PPG-PEG peptide-TNF DNA nanoparticles; PLA 72 KDa-PEG-PPG-PEG TNF DNA nanoparticles, and PLA 72 KDa-PEG-PPG-PEG peptide-TNF DNA nanoparticles.

Figure 11:
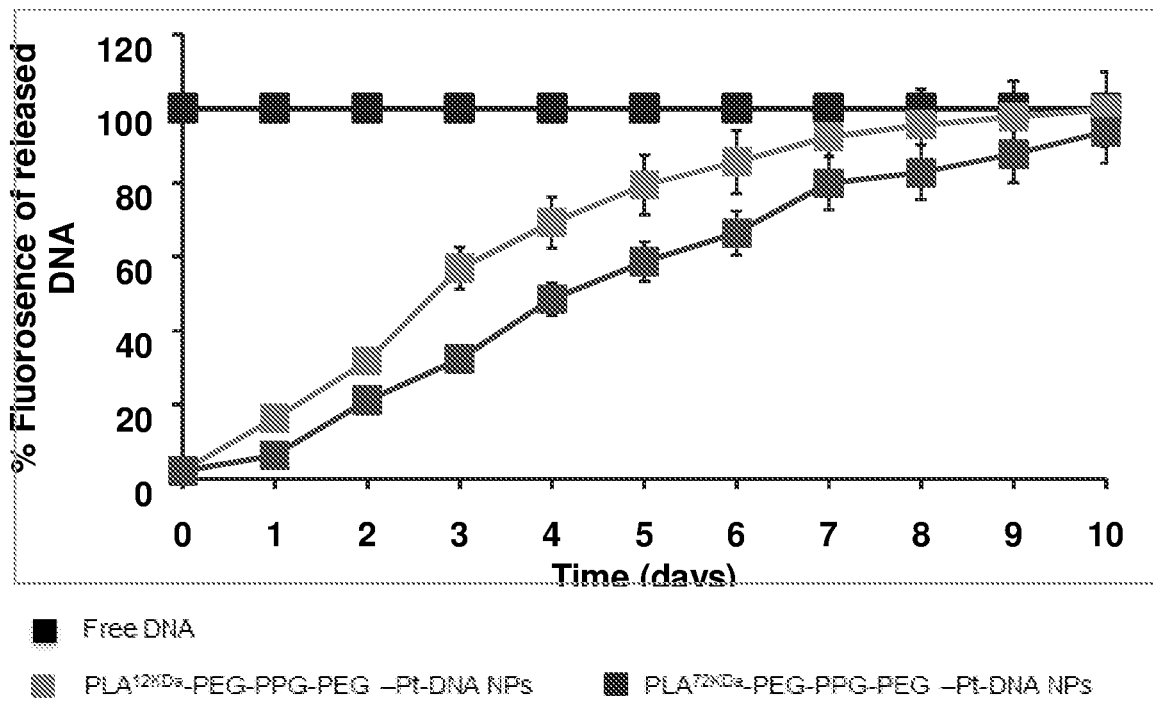

FIG. 11 is a line graph showing a comparison of TNF DNA release profiles in non-physiological buffer (PBS ph 7.4). Percent fluorescence of released DNA (ordinate) is shown as a function of time for two different nanoparticles: PLA 12 KDa-PEG-PPG-PEG peptide-TNF DNA nanoparticles; and PLA 72 KDa-PEG-PPG-PEG peptide-TNF DNA nanoparticles.

DETAILED DESCRIPTION

Provided herein are dual nanoparticles, or a dual nanoparticle (DNP) system, for use in driving expression of inflammatory cytokines in tumor cells. The DNP system consists of a di-block polymeric NP that surrounds a smaller cationic nanocomplex. Data show that the polymeric NP released the cationic nanocomplex within the tumor cell. In turn, the cationic nanocomplex entered the nucleus and induced the expression of exogenous genes, for example genes that expressed cytokines. In various embodiments, TNF was used based on its pleotropic inflammatory and anti-cancer activities. Examples demonstrate that the DNP system was highly effective in driving expression of cytokines such as TNF in tumor cells. Data show that the DNPs were active in inducing apoptosis of tumors in mouse models. These DNPS were capable of promoting anti-tumor immunity by the selective expression of inflammatory cytokines. In sum, data demonstrate that this approach is highly effective in conferring anti-tumor activity in the absence of toxicity. The examples further indicate that this DNP system is broadly applicable for cytokines that promote immune recognition and destruction.

The therapeutic strategy of expressing exogenous genes in tumors growing in vivo has been substantially curtailed by the lack of effective delivery systems (Yin H. et al., 2014 Nature Rev. Genetics, 15, pages 541-555; Amer M. H., 2014 Mol Cell Ther. 2014; 2: 27, pages 1-19; Collins M. et al., 2015 Proc. Biol. Sci. 22; 282(1821):20143003. doi: 10.1098/rspb.2014.3003). One of the major challenges has been delivering cationic DNA complexes to tumor cells at sufficient levels to significantly affect the tumor phenotype (Kircheis R. et al., 2002 Cancer Gene Ther. 9(8), pages 673-680). To address this obstacle in part, novel polymeric NPs have been developed with high molecular weight PLA for the systemic delivery of peptide cargoes to tumor cells (Kumar M. et al., 2014 ISRN Nanotechnology Volume 2014 (2014), Article ID 939378, 12 pages; Hasegawa M. et al., 2015 Clin Cancer Res. 21(10), pages 2338-2347. doi: 10.1158/1078-0432.CCR-14-3000. Epub 2015 Feb. 23). Additionally, for effective DNA delivery, a linear short histidine- and cysteine-modified arginine (HCR) peptide was developed that maintains DNA condensation, imparts endosomal escape properties and directs nuclear localization (Mann A. et al., 2014 Mol. Pharmaceutics, 11 (3), pages 683-696).

Examples herein demonstrate that, using novel HCR peptide, one could successfully generate cationic peptide-DNA nanocomplexes (NCs). Moreover, these ~80 nm NCs were successfully encapsulated in ~200 nm polymeric NPs to circumvent degradation of the NCs in plasma. Degradation of nanoparticles in plasma which has been a significant hurdle in gene delivery systems (Yin H et al., 2014 Nature Reviews Genetics 15, pages 541-555; Amer M. H., 2014 Mol Cell Ther. 2014; 2: 27, pages 1-19; et al., 2015 Proc. Biol. Sci. 22; 282(1821):20143003. doi: 10.1098/rspb.2014.3003).

A "nanoparticle in a nanoparticle" or dual NP system for gene delivery was utilized in Examples herein. In assessing the effectiveness of this system, NP/NCs were generated by incorporation of the green fluorescent protein (GFP) gene as a prototype model. Indeed, data showed that treatment of MCF-7 cells with the NP/GFP-NCs is associated with GFP expression, indicating that the HCR peptide-DNA NC functions in driving the exogenous GFP gene. The encapsulation of polymer-doxorubicin NPs (~80 nm) into 2500 nm silica microparticles was utilized for the delivery of doxorubicin to tumors (Xu R. et al., 2016 Nature Biotechnology 34, pages 414-418). This "nanoparticle in a nanoparticle" is thus larger than the ~200 nm NP/NCs and provides the potential of dual NPs for the delivery of DNA, as well as certain anti-cancer agents, into tumor cells.

Another obstacle for the delivery of DNA vectors is often the need to achieve high transfection or transduction efficiencies of the tumor cell population to have a significant therapeutic impact. This obstacle can be circumvented by the expression of a secreted protein, and is particularly applicable to reprogramming of the tumor microenvironment. In this context, TNF is a pleiotropic cytokine that promotes immune surveillance and directly kills cancer cells (Brenner D. et al., 2015 Nature Reviews Immunology 15, pages 362-374). Despite the promise of TNF as an antitumor agent, systemic TNF-induced toxicity precluded clinical development of this cytokine, other than in the setting of isolated limb perfusion for sarcomas (Jakob J. et al., 2016 Cancer doi: 10.1002/cncr.29991). Noteworthy, however, are the findings that intratumoral administration of TNFerade has activity in the treatment of diverse human cancers (Weichselbaum R. et al., 2009 Cancer Gene Therapy 16, pages 609-619), supporting the premise that a system for the delivery of TNF to tumors, while circumventing the systemic toxicity, could be an effective anti-cancer therapy. Accordingly, dual NP/NCs were constructed that express the pE425-TNF vector. The pE425 promoter is activated by ROS in the response of tumor cells to radiation and chemotherapy (Ibid.). In addition, the pE425 promoter is selectively activated in cancer cells with increased ROS levels (Gorrini C. et al., 2013 Nat Rev Drug Discov. December; 12(12):931-947) and the production of TNF further drives ROS production in an auto inductive process (Blaser H, 2016 Trends Cell Biol 26(4), pages 249-261). Thus, the pE425-TNF vector is particularly well suited for the induction of TNF in tumors. Systemic NP/TNF-NC treatment of Ehrlich breast tumors is associated with production of TNF, induction of apoptosis and inhibition of growth. Interestingly, similar effects were observed when the NP/TNF-NCs were administered intratumorally, indicating that this dual NP system can be given systemically or directly into tumors. Moreover and importantly, the NP/TNF-NCs induced little if any systemic toxicity.

The dual NP/NC system reported here has certain potential advantages for cancer treatment. For instance, the NP/TNF-NCs could be administered systemically or locally in combination with radiation and/or chemotherapy (Weichselbaum R. et al., 2009 Cancer Gene Therapy 16, pages 609-619). In addition, treatment of tumors with NP/TNF-NCs could be used to reprogram the immune microenvironment. In this way, NP/TNF-NCs could convert "cold" to "hot" tumors and be combined with immune checkpoint inhibitors. This dual NP system could also be employed to reprogram immune surveillance in tumors by incorporating genes encoding cytokines, such as IL-12 and others, under control of the pE425 promoter.

The present disclosure provides a composition comprising nanoparticles (also referred to herein as "NPs") loaded with cytokines (e.g., TNF). TNF is involved in tumor cell necrosis. Inhibition of the activity of TNF protein reduces cancer cell survival and proliferation. Delivery of a cytokine such as TNF to the intracellular space of cancer cells is facilitated by NPs. Accordingly, the present disclosure provides methods for treating a disease, such as cancer, by administering a composition comprising the NPs loaded with a peptide or a polynucleotide that induces tumor necrosis. Methods for producing the composition are also provided.

Nanoparticles (also referred to herein as "NPs") can be produced as nanocapsules or nanospheres. Protein loading in the nanoparticle can be carried out by either the adsorption process or the encapsulation process (Spada et al., 2011; Protein delivery of polymeric nanoparticles; World Academy of Science, Engineering and Technology: 76). Nanoparticles, by using both passive and active targeting strategies, can enhance the intracellular concentration of drugs in cancer cells while avoiding toxicity in normal cells. When nanoparticles bind to specific receptors and enter the cell, they are usually enveloped by endosomes via receptor-mediated endocytosis, thereby bypassing the recognition of P-glycoprotein, one of the main drug resistance mechanisms (Cho et al., 2008, Therapeutic Nanoparticles for Drug Delivery in Cancer, Clin. Cancer Res., 2008, 14:1310-1316). Nanoparticles are removed from the body by opsonization and phagocytosis (Sosnik et al., 2008; Polymeric Nanocarriers: New Endeavors for the Optimization of the Technological Aspects of Drugs; Recent Patents on Biomedical Engineering, 1: 43-59). Nanocarrier based systems can be used for effective drug delivery with the advantages of improved intracellular penetration, localized delivery, protect drugs against premature degradation, controlled pharmacokinetic and drug tissue distribution profile, lower dose requirement and cost effectiveness (Farokhzad O C, et al.; Targeted nanoparticle-aptamer bioconjugates for cancer chemotherapy in vivo. Proc. Natl. Acad. Sci. USA 2006, 103 (16): 6315-20; Fonseca C, et al., Paclitaxel-loaded PLGA nanoparticles: preparation, physicochemical characterization and in vitro anti-tumoral activity. J. Controlled Release 2002; 83 (2): 273-86; Hood et al., Nanomedicine, 2011, 6(7):1257-1272).

The uptake of nanoparticles is indirectly proportional to their small dimensions. Due to their small size, the polymeric nanoparticles have been found to evade recognition and uptake by the reticulo-endothelial system (RES), and can thus circulate in the blood for an extended period (Borchard et al., 1996, Pharm. Res. 7: 1055-1058). Nanoparticles are also able to extravasate at the pathological site like the leaky vasculature of a solid tumor, providing a passive targeting mechanism. Due to the higher surface area leading to faster solubilization rates, nano-sized structures usually show higher plasma concentrations and area under the curve (AUC) values. Lower particle size helps in evading the host defense mechanism and increase the blood circulation time. Nanoparticle size affects drug release. Larger particles have slower diffusion of drugs into the system. Smaller particles offer larger surface area but lead to fast drug release. Smaller particles tend to aggregate during storage and transportation of nanoparticle dispersions. Hence, a compromise between a small size and maximum stability of nanoparticles is desired. The size of nanoparticles used in a drug delivery system should be large enough to prevent their rapid leakage into blood capillaries but small enough to escape capture by fixed macrophages that are lodged in the reticuloendothelial system, such as the liver and spleen.

In addition to their size, the surface characteristics of nanoparticles are also an important factor in determining the life span and fate during circulation. Nanoparticles should ideally have a hydrophilic surface to escape macrophage capture. Nanoparticles formed from block copolymers with hydrophilic and hydrophobic domains meet these criteria. Controlled polymer degradation also allows for increased levels of agent delivery to a diseased state. Polymer degradation can also be affected by the particle size. Degradation rates increase with increase in particle size in vitro (Biopolymeric nanoparticles; Sundar et al., 2010, Science and Technology of Advanced Materials; doi:10.1088/1468-6996/11/1/014104).

Poly(lactic acid) (PLA) has been approved by the US FDA for applications in tissue engineering, medical materials and drug carriers and poly(lactic acid)-poly(ethylene glycol) PLA-PEG based drug delivery systems are known in the art. US2006/0165987A1 describes a stealthy polymeric biodegradable nanosphere comprising poly(ester)-poly(ethylene) multiblock copolymers and optional components for imparting rigidity to the nanospheres and incorporating pharmaceutical compounds. US2008/0081075A1 discloses a novel mixed micelle structure with a functional inner core and hydrophilic outer shells, self-assembled from a graft macromolecule and one or more block copolymer. US2010/0004398A1 describes a polymeric nanoparticle of shell/core configuration with an interphase region and a process for producing the same.

In various embodiments, the invention further comprises a cationic molecule that interacts with a therapeutic molecule (e.g., an isolated nucleic acid that encodes TNF-α protein) to form a stable nanocomplex and/or serves as a cell penetrating peptide. In various embodiments, the cationic molecule cell comprises a penetrating peptide comprises or a protein transduction domain. In various embodiments, the cationic molecule is a cationic peptide that facilitates transduction of the therapeutic agent (e.g., DNA and a vector) to the nucleus.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art. The terms used throughout this specification are defined as follows, unless otherwise limited in specific instances.

The articles "a," "an" and "the" are used to refer to one or to more than one (i.e., to at least one) of the grammatical object of the article.

The terms "comprise" "comprising" "including" "containing" "characterized by" and grammatical equivalents thereof are used in the inclusive, open sense, meaning that additional elements may be included. It is not intended to be construed as "consists of only."

As used herein, "consisting of" and grammatical equivalent thereof exclude any element, step or ingredient not specified in the claim.

As used herein, the term "about" or "approximately" usually means within 20%, more preferably within 10%, and most preferably still within 5% of a given value or range.

The term "biodegradable" as used herein refers to both enzymatic and non-enzymatic breakdown or degradation of the polymeric structure.

TABLE 1

Examples of cationic molecules that are cell penetrating peptides

| Name of cell penetrating molecule | Description/comments | Amino acid Sequence | SEQ ID NO: |
|---|---|---|---|
| Penetratin | Antennapedia (43-58) | RQIKIWFQNRRMKWKK | 1 |
| Tat peptide | Tat (48-60) | GRKKRRQRRRPPQ | |
| pVEC | Cadherin (615-632) | LLIILRRRIRKQAHAHSK | 2 |
| Transportan | Galanine/Mastoparan | GWTLNSAGYLLGKINLKALAALA KKIL | 3 |
| MPG | HIV-gp41 | GALFLGFLGAAGSTMGAWSQPKK KRKV | 4 |
| Pep-1 | HIV-RT | KETWWETWWTEWSQPKKKRKV | 5 |
| Polyarginines | Based on Tat peptide | $(R)_n$, 6 < n < 12 [e.g., 9Rs = RRRRRRRRR] | NA |
| MAP | de novo | KLALKLALKALKAALKLA | 6 |
| $R_6W_3$ | Based on penetratin | RRWWRRWRR | 7 |
| $CR_5H_7R_4C$ Cys-cyclized | C-cyclized Poly-cationic peptide | CRRRRRHHHHHHHRRRRC | 8 |

The term "cationic" refers to any agent, composition, molecule or material that has a net positive charge or positive zeta potential under the respective environmental conditions. In various embodiments, nanoparticles described herein include a cationic polymer, peptide, protein carrier, or lipid.

The term "cell-penetrating" refers to an peptide, protein, fragment, or variant thereof that is transported across the cell membrane (i.e., into the cytoplasm) of cells. The cell penetrating peptide or protein may be part of a large molecule (e.g., an immunoglobulin). In various embodiments, the cell penetrating peptide, protein, fragment or variant thereof is effective for transporting a nanoparticle, therapeutic agent/nanoparticle and/or complex/nanoparticle into the cytoplasm of the cells without the aid of a carrier or conjugate. In some embodiments, the antibody, fragment, or variant thereof is contacting, bound or conjugated to the therapeutic agent and//or nanoparticle As used herein, the term "nanoparticle" refers to particles in the range between 10 nm to 1000 nm in diameter, wherein diameter refers to the diameter of a perfect sphere having the same volume as the particle. The term "nanoparticle" is used interchangeably as "nanoparticle(s)". In some cases, the diameter of the particle is in the range of about 1-1000 nm, 10-500 nm, 20-300 nm, or 100-300 nm. In various embodiments, the diameter is about 30-120 nm.

In some cases, a population of particles may be present. As used herein, the diameter of the nanoparticles is an average of a distribution in a particular population.

As used herein, the term "polymer" is given its ordinary meaning as used in the art, i.e., a molecular structure comprising one or more repeat units (monomers), connected by covalent bonds. The repeat units may all be identical, or in some cases, there may be more than one type of repeat unit present within the polymer.

The term "nucleic acid" refers to polynucleotides such as deoxyribonucleic acid (DNA), ribonucleic acid (RNA), its variants and derivatives thereof.

As used herein, the term "therapeutic agent" and "drug" are used interchangeably and are also intended to encompass not only compounds or species that are inherently pharmaceutically or biologically active, but materials which include one or more of these active compounds or species, as well as conjugations, modification, and pharmacologically active fragments, and antibody derivatives thereof.

A "targeting moiety" is a molecule that will bind selectively to the surface of targeted cells. For example, the targeting moiety may be a ligand that binds to the cell surface receptor found on a particular type of cell or expressed at a higher frequency on target cells than on other cells.

As used herein, the term "complexed" refers to placing an isolated nucleic acid provided herein with a cationic-cell penetrating peptide provided herein under conditions that allow the formation of a nucleic acid-peptide complex. The term "complex" refers to an isolated nucleic acid provided herein conjugated to a cationic cell-penetrating peptide. A non-limiting example of the conditions that allow formation of a nucleic acid-peptide complex is set forth in Example 13 below.

The targeting moiety or therapeutic agent can be a peptide or protein. "Proteins" and "peptides" are well-known terms in the art, and as used herein, these terms are given their ordinary meaning in the art. Generally, peptides are amino acid sequences of less than about 100 amino acids in length, but can include up to 300 amino acids. Proteins are generally considered to be molecules of at least 100 amino acids. The amino acids can be in D- or L-configuration. A protein can be, for example, a protein drug, an antibody, a recombinant antibody, a recombinant protein, an enzyme, or the like. In some cases, one or more of the amino acids of the peptide or protein can be modified, for example by the addition of a chemical entity such as a carbohydrate group, a phosphate group, a farnesyl group, an isofarnesyl group, a fatty acid group, a linker for conjugation, functionalization, or other modification such as cyclization, by-cyclization and any of numerous other modifications intended to confer more advantageous properties on peptides and proteins. In other instances one or more of the amino acids of the peptide or protein can be modified by substitution with one or more non-naturally occurring amino acids. The peptides or proteins may by selected from a combinatorial library such as a phage library, a yeast library, or an in vitro combinatorial library.

As used herein, the term "antibody" refers to any molecule incorporating an amino acid sequence or molecule with secondary or tertiary structural similarity conferring binding affinity to a given antigen that is similar or greater to the binding affinity displayed by an immunoglobulin variable region containing molecule from any species. The term antibody includes, without limitation native antibodies consisting of two heavy chains and two light chains; binding molecules derived from fragments of a light chain, a heavy chain, or both, variable domain fragments, heavy chain or light chain only antibodies, or any engineered combination of these domains, whether monospecific or bispecific, and whether or not conjugated to a second diagnostic or therapeutic moiety such as an imaging agent or a chemotherapeutic molecule. The term includes without limitation immunoglobulin variable region derived binding moieties whether derived from a murine, rat, rabbit, goat, llama, camel, human or any other vertebrate species. The term refers to any such immunoglobulin variable region binding moiety regardless of discovery method (hybridoma-derived, humanized, phage derived, yeast derived, combinatorial display derived, or any similar derivation method known in the art), or production method (bacterial, yeast, mammalian cell culture, or transgenic animal, or any similar method of production known in the art).

The term "combination," "therapeutic combination," or "pharmaceutical combination" as used herein refer to the combined administration of two or more therapeutic agents (e.g., co-delivery).

The term "cytokine" is a generic term for proteins that are released by one cell population and that act on another cell population as intercellular mediators. Examples of such cytokines are lymphokines, monokines, and traditional polypeptide hormones. Included among the cytokines are growth hormones, such as human growth hormone, N-methionyl human growth hormone, and bovine growth hormone; parathyroid hormone; thyroxine; insulin; proinsulin; relaxin; prorelaxin; glycoprotein hormones, such as follicle stimulating hormone (FSH), thyroid stimulating hormone (TSH), and luteinizing hormone (LH); hepatic growth factor; fibroblast growth factor; prolactin; placental lactogen; a tumor necrosis factor such as tumor necrosis factor-alpha (TNF-$\alpha$) and tumor necrosis factor-beta (TNF-$\beta$); mullerian-inhibiting substance; mouse gonadotropin-associated peptide; inhibin; activin; vascular endothelial growth factor; integrin; thrombopoietin (TPO); nerve growth factors such as NGF-alpha (NGF-$\alpha$); platelet-growth factor; placental growth factor; transforming growth factors (TGFs) such as TGF-alpha (TGF-$\alpha$) and TGF-beta (TGF-$\beta$); insulin-like growth factor-1 and -11; erythropoietin (EPO); osteoinductive factors; interferons such as interferon-alpha (IFN-α), interferon-beta (IFN-β), and interferon-gamma (IFN-γ); colony stimulating factors (CSFs) such as macrophage-CSF (M-CSF); granulocyte macrophage-CSF (GM-CSF); and granulocyte-CSF (G-CSF); interleukins (ILs) such as IL-1, IL-2, IL-3, IL-4, IL-5, IL-6, IL-7, IL-8, IL-9, IL-10, IL-11, IL-12, IL-13, IL-15, IL-17, IL-18, IL-21, IL-22, IL-23, IL-33; and other polypeptide factors including LIF and kit ligand (KL). As used herein, the term cytokine includes proteins from natural sources or from recombinant cell culture and biologically active equivalents of the native sequence cytokines.

The term "TNF" or "TNF-α" refers to tumor necrosis factor. The biological effects of TNF were first described by Carswel et al., 1979 PNAS 72: pages 3666 as a factor present in serum that was induced by endotoxin, and which caused necrosis of certain types of tumors. More recently, recombinantly produced human TNF has also been shown to be an effective anti-cancer agent (Pannica et al., (Nature (London) (1984) 312:724-729), Shirai et al., (Nature (London) (1985) 313:803), Wang et al., (Science (1985), 228: 149). See also U.S. Pat. No. 8,835,610, which is incorporated herein in its entirety.

The term "human TNF-α" (abbreviated herein as hTNF-α) includes a dimeric cytokine protein. The term includes a homotrimeric protein comprising three 17.5 kD TNF-α proteins. The term human "TNF-α" is intended to include recombinant human TNF-α (TNF-α) which can be prepared by standard recombinant expression methods. The amino acid sequence of human TNF-α (SEQ ID NO: 9) is shown in Table 2. The nucleic acid sequence (SEQ ID NO: 10) and amino acid sequence (SEQ ID NO: 11) of the entire vector encoding the TNF-α is also shown in Table 2; show are the sequences of the whole vector that in various embodiment is encapsulated into the nanoparticles. The TNFα is derived by EGR1-promoter (pE425).

TABLE 2

Nucleotide Sequence and Amino Acid Sequence of TNF-α Encoding Vector, and Amino Acid Sequence of Human TNF-α

| Protein/Vector | Sequence Identifier | Sequence |
|---|---|---|
| | | 123456789012345678901234567890 |
| Human TNF-α amino acid sequence | SEQ ID NO: 9 | VRSSSRTPSDKPVAHVVANPQAEGQLQWLNDR ANALLANGVELRDNQLVVPSEGLYLIYSQVLF KGQGCPSTHVLLTHTISRIAVSYQTKVNLLSA IKSPCQRETPEGAEAKPWYEPIYLGGVFQLEK GDRLSAEINRPDYLDFAESGQVYFGIIAL |
| entire vector amino acid sequence including the human TNF-α portion | SEQ ID NO: 10 | MSTESMIRDVELAEEALPKKTGGPQGSRRCLF LSLFSFLIVAGATTLFCLLHFGVIGPQREEFP RDLSLISPLAQAVRSSSRTPSDKPVAHVVANP QAEGQLQWLNRRANALLANGVELRDNQLVVPS EGLYLIYSQVLFKGQGCPSTHVLLTHTISRIA VSYQTKVNLLSAIKSPCQRETPEGAEAKPWYE PIYLGGVFQLEKGDRLSAEINRPDYLDFAESG QVYFGIIAL |
| entire vector nucleic acid sequence | SEQ ID NO: 11 | cagacgctccctcagcaaggacagcagaggac cagctaagagggagagaagcaactacagaccc ccctgaaaacaaccctcagacgccacatccc ctgacaagctgccaggcaggttctcttcctct cacatactgacccacggctccaccctctctcc cctggaaaggacaccatgagcactgaaagcat gatccgggacgtggagctggccgaggaggcgc tccccaagaagacaggggggcccagggctcc aggcggtgcttgttcctcagcctcttctcctt cctgatcgtggcaggcgccaccacgctcttct gcctgctgcactttggagtgatcggcccccag agggaagagttccccagggacctctctctaat cagccctctggcccaggcagtcagatcatctt ctcgaacccgagtgacaagcctgtagcccat gttgtagcaaaccctcaagctgaggggcagct ccagtggctgaaccgccgggccaatgccctcc tggccaatggcgtggagctgagagataaccag ctggtggtgccatcagagggcctgtacctcat ctactcccaggtcctcttcaagggccaaggct gcccctccacccatgtgctcctcacccacacc atcagccgcatcgccgtctcctaccagaccaa ggtcaacctcctctctgccatcaagagccct gccagagggagacccagaggggctgaggcc aagccctggtatgagcccatctatctgggagg ggtcttccagctggagaagggtgaccgactca gcgctgagatcaatcggcccgactatctcgac tttgccgagtctgggcaggtctactttgggat cattgccctgtgaggaggacgaacatccaacc ttcccaaacgcctccctgccccaatcccttt attaccccctccttcagacaccctcaacctct tctggctcaaaaagagaattgggggcttaggg tcggaacccaagcttagaactttaagcaacaa gaccaccacttcgaaacctgggattcaggaat gtgtggcctgcacagtgaagtgctggcaacca ctaagaattcaaactggggcctccagaactca |

TABLE 2-continued

Nucleotide Sequence and Amino Acid Sequence of TNF-α Encoding
Vector, and Amino Acid Sequence of Human TNF-α

Protein/Vector Sequence Identifier Sequence

```
ctggggcctacagctttgatccctgacatctg
gaatctggagaccagggagcctttggttctgg
ccagaatgctgcaggacttgagaagacctcac
ctagaaattgacacaagtggaccttaggcctt
cctctctccagatgtttccagacttccttgag
acacggagcccagccctccccatggagccagc
tccctctatttatgtttgcacttgtgattatt
tattatttatttattatttatttatttacaga
tgaatgtatttatttgggagaccggggtatcc
tgggggacccaatgtaggagctgccttggctc
agacatgttttccgtgaaaacggagctgaaca
ataggctgttcccatgtagcccccctggcctct
gtgccttcttttgattatgttttttaaaatat
ttatctgattaagttgtctaaacaatgctgat
ttggtgaccaactgtcactcattgctgagcct
ctgctcccaggggagttgtgtctgtaatcgc
cctactattcagtggcgagaaataaagtttgc
ttagaaaagaaaaaaaaaaaa
```

The term "pharmaceutically acceptable" as used herein refers to those compounds, materials, compositions and/or dosage forms, which are, within the scope of sound medical judgment, suitable for contact with the tissues a warm-blooded animal, e.g., a mammal or human, without excessive toxicity, irritation allergic response and other problem complications commensurate with a reasonable benefit/risk ratio.

A "therapeutically effective amount" of a polymeric nanoparticle comprising one or more therapeutic agents is an amount sufficient to provide an observable or clinically significant improvement over the baseline clinically observable signs and symptoms of the disorders treated with the combination.

The term "subject" or "patient" as used herein is intended to include animals, which are capable of suffering from or afflicted with a cancer or any disorder involving, directly or indirectly, a cancer. Examples of subjects include mammals, e.g., humans, apes, monkeys, dogs, cows, horses, pigs, sheep, goats, cats, mice, rabbits, rats, and transgenic non-human animals. In an embodiment, the subject is a human, e.g., a human suffering from, at risk of suffering from, or potentially capable of suffering from cancers.

The term "treating" or "treatment" as used herein comprises a treatment relieving, reducing or alleviating at least one symptom in a subject or producing a delay in the progression of a disease. For example, treatment can be the diminishment of one or several symptoms of a disorder or complete eradication of a disorder, such as cancer. Within the meaning of the present disclosure, the term "treat" also denotes to arrest and/or reduce the risk of worsening a disease. The term "prevent", "preventing" or "prevention" as used herein comprises the prevention of at least one symptom associated with or caused by the state, disease or disorder being prevented.

As used herein, the term "refractory" to a therapeutic agent when referring to a cancer patient or tumor means that the cancer or tumor has innate, or achieved resistance to, the effects of the therapeutic agent as a result of contact with the therapeutic agent. Stated alternatively, the cancer is resistant to the ordinary standard of care associated with the particular therapeutic agent. In some embodiments, the methods of treating cancer described herein comprise a PD-1 refractory tumor.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

Polymeric Nanoparticles

Provided herein are biodegradable polymeric nanoparticles for the delivery of one or more therapeutics such as a cytokine, or a plasmid or DNA encoding the cytokine.

Thus, in an aspect, provided herein is a polymeric nanoparticle comprising a cytokine or portion thereof or an isolated nucleic acid that encodes the cytokine or portion thereof.

In another aspect, provided herein is a polymeric nanoparticle comprising a TNF-α protein comprising the amino acid sequence at least 70% identical to the sequence of SEQ ID NO: 9, or a portion thereof, or an isolated nucleic acid that encodes a TNF-α protein comprising the amino acid sequence at least 70% identical to the sequence of SEQ ID NO: 9, or a portion thereof.

In an embodiment, the polymeric nanoparticles provided herein comprise a block copolymer comprising poly(lactic acid) (PLA) and poly(ethylene glycol) (PEG). Poly(lactic acid) (PLA), is a hydrophobic polymer, and is a preferred polymer for synthesis of the polymeric nanoparticles. However, poly(glycolic acid) (PGA) and block copolymer of poly lactic acid-co-glycolic acid (PLGA) may also be used. The hydrophobic polymer can also be biologically derived or a biopolymer. The molecular weight of the PLA used is generally in the range of about 2,000 g/mol to 80,000 g/mol. Thus, in an embodiment, the PLA used is in the range of about 10,000 g/mol to 80,000 g/mol. The average molecular weight of PLA may also be about 70,000 g/mol.

PEG is another preferred component to of the polymer used to form the polymeric nanoparticles as it imparts hydrophilicity, anti-phagocytosis against macrophage, and resistance to immunological recognition. Block copolymers like poly(ethylene glycol)-poly(propylene glycol)-poly(ethylene glycol) (PEG-PPG-PEG) are hydrophilic or hydrophilic-hydrophobic copolymers that can be used in the present invention. Block copolymers may have two, three, four, or more numbers of distinct blocks.

As used herein, one g/mole is equivalent to one "dalton" (i.e., dalton and g/mol are interchangeable when referring to the molecular weight of a polymer). "Kilodalton" as used herein refers to 1,000 daltons.

In a further embodiment, the polymeric nanoparticles provided herein comprise poly(lactic acid)-poly(ethylene glycol) (PLA-PEG) di-block copolymer.

In yet a further embodiment, the polymeric nanoparticles provided herein comprise poly(lactic acid)-poly(ethylene glycol)-poly(propylene glycol)-poly(ethylene glycol) (PLA-PEG-PPG-PEG) tetra-block copolymer. In various embodiments, the nanoparticles comprise a NANOPRO™, which is a biodegradable, long blood circulating, stealth, tetra-block polymeric nanoparticle platform (NanoProteagen Inc.; Massachusetts). The PLA-PEG-PPG-PEG tetra-block copolymer can be formed from chemical conjugation of PEG-PPG-PEG tri-block copolymer with PLA.

The synthesis and characterization of nanoparticles comprising poly(lactic acid)-poly(ethylene glycol)-poly(propylene glycol)-poly(ethylene glycol) (PLA-PEG-PPG-PEG) tetra block copolymer are described in PCT publication no. WO2013/160773, which is hereby incorporated by reference in its entirety. Polymeric nanoparticles comprising poly(lactic acid)-poly(ethylene glycol)-poly(propylene glycol)-poly(ethylene glycol) (PLA-PEG-PPG-PEG) tetra block copolymer have been shown to be safe, stable and non-toxic. The process used to form this tetra-block copolymer comprises covalently attaching PEG-PPG-PEG to the poly-lactic acid (PLA) matrix, resulting in the block copolymer becoming a part of the matrix, i.e., the nanoparticle delivery system (see Example 21). This prevents leaching out of emulsifier into the medium.

In some embodiments, the average molecular weight (Mn) of the hydrophilic-hydrophobic block copolymer (e.g., PEG-PPG-PEG) is generally in the range of 1,000 to 20,000 g/mol. In a further embodiment, the average molecular weight (Mn) of the hydrophilic-hydrophobic block copolymer is about 4,000 g/mol to 15,000 g/mol. In some cases, the average molecular weight (Mn) of the hydrophilic-hydrophobic block copolymer is 4,400 g/mol, 8,400 g/mol, or 14,600 g/mol.

A block copolymer of the instant invention can consist essentially of a segment of poly(lactic acid) (PLA) and a segment of poly(ethylene glycol)-poly(propylene glycol)-poly(ethylene glycol) (PEG-PPG-PEG).

A specific biodegradable polymeric nanoparticle of the instant invention is formed of the block copolymer poly(lactic acid)-poly(ethylene glycol)-poly(propylene glycol)-poly(ethylene glycol) (PLA-PEG-PPG-PEG).

Another specific biodegradable polymeric nanoparticle of the instant invention is formed of the block copolymer poly(lactic acid)-poly(ethylene glycol)-poly(propylene glycol)-poly(ethylene glycol)-poly(lactic acid) (PLA-PEG-PPG-PEG-PLA).

The biodegradable polymers of the instant invention can be formed by chemically modifying PLA with a hydrophilic-hydrophobic block copolymer using a covalent bond.

The biodegradable polymeric nanoparticles of the instant invention have, in various embodiments, a size in the range of about 30-300 nm, a size of about 100-300 nm, or a size of about 100-250 nm, or a size of at least about 100 nm.

The biodegradable polymeric nanoparticles of the instant invention have, in various embodiments, a size in the range of about 30-120 nm, a size of about 120-200 nm, or a size of about 200-260 nm, or a size of at least about 260 nm.

In an embodiment, the biodegradable polymer of the instant invention is substantially free of emulsifier, or may comprise external emulsifier by an amount of about 0.5% to 5% by weight.

In an embodiment, the biodegradable polymeric nanoparticle of the present invention is PLA-PEG-PPG-PEG, and the average molecular weight of the poly(lactic acid) block is about 60,000 g/mol, the average weight of the PEG-PPG-PEG block is about 8,400 or about 14,600 g/mol, and the external emulsifier is about 0.5% to 5% by weight.

In another embodiment, the biodegradable polymeric nanoparticle of the present invention is PLA-PEG-PPG-PEG, and the average molecular weight of the poly(lactic acid) block is less than or equal to approximately 16,000 g/mol, the average weight of the PEG-PPG-PEG block is about 8,400 g/mol or about 14,600 g/mol, and wherein the composition is substantially free of emulsifier.

In an embodiment, the biodegradable polymeric nanoparticle of the present invention is PLA-PEG-PPG-PEG, and the average molecular weight of the poly(lactic acid) block is about 72,000 g/mol (or 72 kDa), the average weight of the PEG-PPG-PEG block is about 8,400 or about 14,600 g/mol, and the external emulsifier is about 0.5% to 5% by weight. In another embodiment, the biodegradable polymeric nanoparticle of the present invention is PLA-PEG-PPG-PEG, and the average molecular weight of the poly(lactic acid) block is less than or equal to approximately 12,000 g/mol (or 12 kDa), the average weight of the PEG-PPG-PEG block is about 8,400 g/mol or about 14,600 g/mol, and wherein the composition is substantially free of emulsifier.

In an embodiment of the polymeric nanoparticles, the TNF-α protein, or a portion thereof, comprises an amino acid sequence at least 70%, 75%, 80%, 85%, 90%, 95%, or 99% identical to SEQ ID NO: 9.

In another embodiment, the isolated nucleic acid encodes the TNF-α protein, or a portion thereof, that comprises an amino acid sequence at least 70%, 75%, 80%, 85%, 90%, 95%, or 99% identical to SEQ ID NO: 9.

In another embodiment, the polymeric nanoparticles provided herein further comprise a cationic peptide.

In yet another embodiment, the polymeric nanoparticles provided herein further comprise a cell-penetrating peptide.

In another embodiment, the polymeric nanoparticles provided herein further comprise a cationic cell-penetrating peptide. In an embodiment, the cationic, cell-penetrating, or cationic cell-penetrating peptide comprises an amino acid sequence selected from the group consisting of SEQ ID NOs: 1, 2, 3, 4, 5, 6, 7, 8, and polyarginine. Further description of these peptides is found in Table 1.

In a specific embodiment, the polymeric nanoparticles provided herein further comprise a C-cyclized poly-cationic peptide (SEQ ID NO: 8).

In another embodiment, the cationic, cell-penetrating, or cationic cell-penetrating peptide and the isolated nucleic acid (e.g., an isolated nucleic acid that encodes a TNF-α protein) form a complex.

In another aspect, provided herein is a polymeric nanoparticle formed of a polymer consisting essentially of a PLA-PEG-PPG-PEG tetra-block copolymer or PLA-PEG di-block copolymer, wherein the polymeric nanoparticles are loaded with a cytokine, or a portion thereof, or an isolated nucleic acid that encodes for the cytokine, or a portion thereof. In an embodiment, the cytokine is at least 70% identical to the sequence of SEQ ID NO: 9.

In another embodiment, the isolated nucleic acid is complexed (i.e., forms a complex) with a cationic cell-penetrating peptide.

In a further embodiment, the cationic cell-penetrating peptide is selected from the group consisting of SEQ ID NOs: 1, 2, 3, 4, 5, 6, 7, 8, and polyarginine.

In another aspect, provided herein is a complex comprising
 a) an isolated nucleic acid that encodes a TNF-α protein comprising the amino acid sequence at least 70% identical to the sequence of SEQ ID NO: 9, or a portion thereof; and
 b) a cationic, cell-penetrating, or cationic cell-penetrating peptide.

In an embodiment, the cationic, cell-penetrating, or cationic cell-penetrating peptide comprises an amino acid sequence selected from the group consisting of SEQ ID NOs: 1, 2, 3, 4, 5, 6, 7, 8, and polyarginine In a specific embodiment, the cationic cell-penetrating peptide comprises a C-cyclized poly-cationic peptide (SEQ ID NO: 8).

In an embodiment, the complex between the peptide and the nucleic acid is formed via an electrostatic interaction. In a further embodiment, the complex is prepared at a charge ratio or Z(±) of about 5 to 15 or at a charge ratio of about 10.0, wherein the charge ratio is the ratio of amino nitrogen ($NH_3^+$) of peptide per phosphate ($PO_4^-$) group of the nucleic acid Preparation of Dual Polymeric Nanoparticles Provided herein are methods/processes for preparing a polymeric nanoparticle comprising one or more therapeutics. The resulting polymeric nanoparticle is not only non-toxic, safe, and biodegradable, but is stable in vivo, has high storage stability and can be safely used in a nanocarrier system or drug delivery system in the field of medicine. In fact, the polymeric nanoparticles provided herein can increase the half-life of the deliverable drug or therapeutic agent in-vivo.

Also provided herein is a process for efficient cytokine loading (or genetic material (e.g., DNA) that encodes for a cytokine) on a biodegradable polymeric nanoparticle to form an effective and targeted drug delivery system which prevents premature degradation of active agents and has a strong potential for use in cancer therapy.

Specifically, provided herein is a process for efficient loading of a peptide comprising TNF-α, or genetic material (e.g., DNA) that encodes TNF-α on a biodegradable polymeric nanoparticle to form an effective and targeted drug delivery nanoparticle system.

Preparation of the Peptide-Nucleic Acid Complex

In an aspect, provided herein is a process for preparing a complex comprising
 a) an isolated nucleic acid that encodes a TNF-α protein comprising the amino acid sequence at least 70% identical to the sequence of SEQ ID NO: 9, or a portion thereof; and
 b) a cationic, cell-penetrating, or cationic cell-penetrating peptide, comprising the steps of
  i) preparing a stock solution of nucleic acid;
  ii) preparing a stock solution of peptide; and
  iii) adding the stock solution of nucleic acid to a stock solution of peptide while vortexing.

In an embodiment, the nucleic acid stock solution is prepared at a concentration of about 20-40 ng/μL.

In another embodiment, stock solution of nucleic acid is added dropwise to the stock solution of peptide.

In an embodiment, the cationic, cell-penetrating, or cationic cell-penetrating peptide comprises an amino acid sequence selected from the group consisting of SEQ ID NOs: 1, 2, 3, 4, 5, 6, 7, 8, and polyarginine In a specific embodiment, the cationic cell-penetrating peptide comprises a C-cyclized poly-cationic peptide (SEQ ID NO: 8).

In an embodiment, the complex between the peptide and the nucleic acid is formed via an electrostatic interaction. In a further embodiment, the complex is prepared at a charge ratio or Z(±) of about 5 to 15 or at a charge ratio of about 10.0, wherein the charge ratio is the ratio of amino nitrogen ($NH_3^+$) of peptide per phosphate ($PO_4^-$) group of the nucleic acid.

In an embodiment, the complexes resulting from this process are monodisperse complexes.

These complexes have dimensions (e.g., ranging from about 30 to about 150 nm) that may be measured using a Transmission Electron Microscope. In suitable embodiments, the diameter of the complexes provided herein will be between about 50 nm and 100 nm in diameter or between about 70 nm and 90 nm. In a further embodiment, the diameter of the complexes provided herein are about 80 nm.

In an embodiment, the complex has a zeta-potential between about +15 mV and +35 mV. In a further embodiment, the complex has a zeta-potential of about +35 mV.

Preparation of the Polymeric Nanoparticles

In another aspect, provided herein is process for preparing a polymeric nanoparticle comprising a complex comprising
   a) an isolated nucleic acid that encodes a TNF-α protein comprising the amino acid sequence at least 70% identical to the sequence of SEQ ID NO: 9, or a portion thereof; and
   b) a cationic, cell-penetrating, or cationic cell-penetrating peptide, comprising the steps of
      i) dissolving a block copolymer in a solvent to form a block copolymer solution; and
      ii) adding the complex to the block copolymer solution to form a solution comprising the complex and the block copolymer.

In an embodiment, the block copolymer is PLA-PEG di-block copolymer.

In an embodiment, the block copolymer is PLA-PEG-PPG-PEG tetra-block copolymer.

In an embodiment, the block copolymer solution of step i) is prepared at a concentration between about 2 mg/m and 10 mg/ml. In a further embodiment, the block copolymer solution of step i) is prepared at a concentration of about 6 mg/ml.

In an embodiment, the process further comprises the step iii) adding the solution of step ii) to a solution comprising a surfactant. In a further embodiment, the solution resulting from step ii) is stirred until stable nanoparticles are formed.

In various embodiments, the polymeric nanoparticles can adopt a non-spherical configuration upon swelling or shrinking.

The nanoparticle in various embodiments is amphiphilic in nature.

The zeta potential and PDI (Polydispersity Index) of the nanoparticles may be calculated (see U.S. Pat. No. 9,149,426).

The polymeric nanoparticles have dimensions (e.g., ranging from about 100 to about 350 nm) that may be measured using a Transmission Electron Microscope. In suitable embodiments, the diameter of the polymeric nanoparticles provided herein will be between about 100 and 350 nm in diameter or between about 100 and 30 nm in diameter or between about 100 and 250 nm. In a further embodiment, the diameter of the polymeric nanoparticles provided herein are about 100 nm, 110 nm, 120, nm, 130 nm, 140 nm, 150 nm, 160 nm, 170 nm, 180 nm, 190 nm, 200 nm, 210 nm, 220 nm, 230 nm, 240 nm, or 250 nm.

In an embodiment, the polymeric nanoparticles comprising a complex have a zeta-potential between about −50 mV and −10 mV. In a further embodiment, the complex has a zeta-potential of about −30 mV.

Specific processes for polymeric nanoparticle formation and uses in pharmaceutical composition are provided herein for purpose of reference. These processes and uses may be carried out through a variety of methods apparent to those of skill in the art.

Compositions

Also provided herein is a composition comprising the biodegradable polymeric nanoparticle for use in medicine and in other fields that employ a carrier system or a reservoir or depot of nanoparticles. The nanoparticles of the present invention can be extensively used in prognostic, therapeutic, diagnostic or theranostic compositions. Suitably, the nanoparticles of the present invention are used for drug and agent delivery (e.g., within a tumor cell), as well as for disease diagnosis and medical imaging in human and animals. Thus, the instant invention provides a method for the treatment of disease using the nanoparticles further comprising a therapeutic agent as described herein. The nanoparticles of the present invention can also be use in other applications such as chemical or biological reactions where a reservoir or depot is required, as biosensors, as agents for immobilized enzymes and the like.

Thus, in an aspect, provided herein is a composition comprising
   a) a polymeric nanoparticle comprising a block copolymer comprising poly(lactic acid) (PLA) and poly(ethylene glycol) (PEG); and
   b) a cytokine or portion thereof or an isolated nucleic acid that encodes the cytokine or portion thereof.

In another aspect, provided herein is a composition comprising
   a) polymeric nanoparticles comprising a block copolymer comprising poly(lactic acid) (PLA) and poly(ethylene glycol) (PEG); and
   b) a TNF-α protein comprising the amino acid sequence at least 70% identical to the sequence of SEQ ID NO: 9, or a portion thereof, or an isolated nucleic acid that encodes a TNF-α protein comprising the amino acid sequence at least 70% identical to the sequence of SEQ ID NO: 9, or a portion thereof.

In an embodiment, the polymeric nanoparticle comprises poly(lactic acid)-poly(ethylene glycol) (PLA-PEG) di-block copolymer.

In an embodiment, the polymeric nanoparticle comprises poly(lactic acid)-poly(ethylene glycol)-poly(propylene glycol)-poly(ethylene glycol) (PLA-PEG-PPG-PEG) tetra-block copolymer.

In a further embodiment, the PLA-PEG-PPG-PEG tetra-block copolymer is formed from chemical conjugation of PEG-PPG-PEG tri-block copolymer with PLA.

In an embodiment, the molecular weight of PLA is between about 10,000 and about 100,000 daltons.

In an embodiment, the TNF-α protein, or a portion thereof, comprises an amino acid sequence at least 70%, 75%, 80%, 85%, 90%, 95%, or 99% identical to SEQ ID NO: 9.

In another embodiment, the isolated nucleic acid encodes the TNF-α protein, or a portion thereof, that comprises an amino acid sequence at least 70%, 75%, 80%, 85%, 90%, 95%, or 99% identical to SEQ ID NO: 9.

In an embodiment, the composition provided herein further comprises a cationic peptide.

In another embodiment, the composition provided herein further comprises a cell-penetrating peptide.

In another embodiment, the composition provided herein further comprises a cationic cell-penetrating peptide.

In an embodiment, the cationic, cell-penetrating, or cationic cell-penetrating peptide comprises an amino acid sequence selected from the group consisting of SEQ ID NOs: 1, 2, 3, 4, 5, 6, 7, 8, and polyarginine.

In a specific embodiment, the compositions provided herein further comprise a C-cyclized poly-cationic peptide (SEQ ID NO: 8).

In another embodiment, the cationic, cell-penetrating, or cationic cell-penetrating peptide and the isolated nucleic acid (e.g., an isolated nucleic acid that encodes a TNF-α protein) form a complex.

In an embodiment, the compositions provided herein further comprise a chemotherapeutic agent or a targeted anti-cancer agent selected from the group consisting of doxorubicin, daunorubicin, decitabine, irinotecan, SN-38, cytarabine, docetaxel, triptolide, geldanamycin, 17-AAG, 5-FU, oxaliplatin, carboplatin, methotrexate, paclitaxel, indenoisoquinolines, and bortezomib.

In an aspect, provided herein is a pharmaceutical composition comprising
    a) polymeric nanoparticles comprising a block copolymer comprising poly(lactic acid) (PLA) and poly(ethylene glycol) (PEG); and
    b) a TNF-α protein comprising the amino acid sequence at least 70% identical to the sequence of SEQ ID NO: 9, or a portion thereof, or an isolated nucleic acid that encodes a TNF-α protein comprising the amino acid sequence at least 70% identical to the sequence of SEQ ID NO: 9, or a portion thereof,
for use in treating a disease selected from the group consisting of cancer, an autoimmune disease, an inflammatory disease, a metabolic disorder, a developmental disorder, a cardiovascular disease, liver disease, an intestinal disease, an infectious disease, an endocrine disease and a neurological disorder.

In an embodiment of the compositions provided herein, the polymeric nanoparticles are formed of a polymer consisting essentially of poly(lactic acid)-poly(ethylene glycol) (PLA-PEG) di-block copolymer.

In an embodiment the compositions provided herein, the polymeric nanoparticles are formed of a polymer consisting essentially of poly(lactic acid)-poly(ethylene glycol)-poly(propylene glycol)-poly(ethylene glycol) (PLA-PEG-PPG-PEG) tetra-block copolymer.

In an embodiment of the compositions provided herein, the polymeric nanoparticles further comprise a targeting moiety attached to the outside of the polymeric nanoparticles, and wherein the targeting moiety is an antibody, peptide, or aptamer.

Suitable pharmaceutical compositions or formulations can contain, for example, from about 0.1% to about 99.9%, preferably from about 1% to about 60%, of the active ingredient(s). Pharmaceutical formulations for enteral or parenteral administration are, for example, those in unit dosage forms, such as sugar-coated tablets, tablets, capsules or suppositories, or ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount may be reached by administration of a plurality of dosage units.

The pharmaceutical compositions can contain, as the active ingredient, one or more of the nanoparticles of the invention in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose (e.g. lactose monohydrate), dextrose, sucrose, sorbitol, mannitol, starches (e.g. sodium starch glycolate), gum acacia, calcium phosphate, alginates, tragacanth, gelatin, calcium silicate, colloidal silicon dioxide, microcrystalline cellulose, polyvinylpyrrolidone (e.g. povidone), cellulose, water, syrup, methyl cellulose, and hydroxypropyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Methods for Treating

Provided herein is a method for treating a disease in a subject in need thereof comprising administering to the subject a therapeutically effective amount of a pharmaceutical composition comprising
    a) a polymeric nanoparticle comprising a block copolymer comprising poly(lactic acid) (PLA) and poly(ethylene glycol) (PEG); and
    b) a cytokine or portion thereof or an isolated nucleic acid that encodes the cytokine or portion thereof.

In an aspect, provided herein is a method for treating a disease in a subject in need thereof comprising administering to the subject a therapeutically effective amount of a pharmaceutical composition comprising
    a) a polymeric nanoparticle formed of a polymer comprising PLA-PEG di-block copolymer; and
    b) a TNF-α protein comprising the amino acid sequence at least 70% identical to the sequence of SEQ ID NO: 9, or a portion thereof, or an isolated nucleic acid that encodes a TNF-α protein comprising the amino acid sequence at least 70% identical to the sequence of SEQ ID NO: 9, or a portion thereof.

In an embodiment of the methods provided herein, the isolated nucleic acid is complexed with a cationic cell-penetrating peptide.

In an embodiment of the methods provided herein, the cationic cell-penetrating peptide is selected from the group consisting of SEQ ID NOs 1, 2, 3, 4, 5, 6, 7, 8 and polyarginine.

In an embodiment of the methods provided herein, the pharmaceutical composition further comprises a chemotherapeutic agent or a targeted anti-cancer agent selected from the group consisting of doxorubicin, daunorubicin, decitabine, irinotecan, SN-38, cytarabine, docetaxel, triptolide, geldanamycin, 17-AAG, 5-FU, oxaliplatin, carboplatin, methotrexate, paclitaxel, indenoisoquinolines, and bortezomib.

In an embodiment of the methods provided herein, the disease is cancer, an autoimmune disease, an inflammatory disease, a metabolic disorder, a developmental disorder, a cardiovascular disease, liver disease, an intestinal disease, an infectious disease, an endocrine disease and a neurological disorder.

In another embodiment, the disease is cancer.

In yet another embodiment, the cancer is breast cancer, prostate cancer, non-small cell lung cancer, metastatic colon cancer, pancreatic cancer, or a hematological malignancy.

In another embodiment, the cancer comprises a PD-1 refractory tumor.

Without being limited by any particular theory, it is envisioned that that a checkpoint inhibitors such as PD-1, PDL-1, CTLA-4, OX-40, 4-1BB may work substantially better when combined with agents that can increase the cytokines concentration in a tumor microenvironment. Therefore, systemic delivery of a therapeutic agent (e.g., TNF DNA or TNF protein) could significantly increase the local concentration of the therapeutic agent in the tumor microenvironment which will attract cytotoxic T lymphocytes (CTLs) in the area and hence sensitize the cell by enhancing the effect of for example PD-1 or other checkpoint inhibitor therapy. For example, it is possible that systemic delivery of a therapeutic agent, such as TNF DNA, will sensitize PD-1 therapy in PD-1 refractory tumors.

In an embodiment of the methods provided herein, the nanoparticles are formed of a polymer consisting essentially of PLA-PEG di-block copolymer.

In an embodiment of the methods provided herein, the nanoparticles are formed of a polymer consisting essentially of PLA-PEG-PPG-PEG tetra-block copolymer.

In an aspect, provided herein is a method for inducing TNF expression in a cell, comprising contacting the cell with an effective amount of polymeric nanoparticles formed of a polymer comprising PLA-PEG di-block copolymer; wherein the polymeric nanoparticles comprise an isolated nucleic acid that encodes a TNF-α protein comprising the amino acid sequence at least 70% identical to the sequence of SEQ ID NO: 9, or a portion thereof.

In an embodiment of the methods provided herein, the isolated nucleic acid is complexed with a cationic cell-penetrating peptide.

In a further embodiment, the cationic cell-penetrating peptide is selected from the group consisting of SEQ ID NOs: 1, 2, 3, 4, 5, 6, 7, 8 and polyarginine.

In an embodiment, the polymeric nanoparticles are formed of a polymer consisting essentially of PLA-PEG di-block copolymer.

In an embodiment, the polymeric nanoparticles are formed of a polymer consisting essentially of PLA-PEG-PPG-PEG tetra-block copolymer.

In an embodiment of any of the methods provided herein, the TNF-α protein, or a portion thereof, comprises an amino acid sequence at least 70%, 75%, 80%, 85%, 90%, 95%, or 99% identical to SEQ ID NO: 9.

In another embodiment of any of the methods provided herein, the isolated nucleic acid encodes the TNF-α protein, or a portion thereof, that comprises an amino acid sequence at least 70%, 75%, 80%, 85%, 90%, 95%, or 99% identical to SEQ ID NO: 9.

The administration of a pharmaceutical composition provided herein may result not only in a beneficial effect with regard to alleviating, delaying progression of or inhibiting the symptoms, but also in further surprising beneficial effects, e.g. fewer side-effects, more durable response, an improved quality of life or a decreased morbidity, compared with, for example, delivering the agent without using the polymeric nanoparticle system described herein or by any other conventional means.

The effective dosage of the polymeric nanoparticles provided herein may vary depending on the particular protein, nucleic acid, and or other therapeutic agent employed, the mode of administration, the condition being treated, and the severity of the condition being treated. Thus, the dosage regimen of the polymeric nanoparticle is selected in accordance with a variety of factors including the route of administration and the renal and hepatic function of the patient.

Polymeric Nanoparticles Comprising Pharmaceutical Combinations

The polymeric nanoparticle described herein can be used to deliver pharmaceutical combinations. For example, a pharmaceutical combination that can be delivered by the dual nanoparticle system disclosed herein comprises a chemotherapeutic drug and a cytokine or genetic material that encodes a cytokine (e.g., a peptide comprising TNF-α or genetic material that encodes TNF-α).

In an aspect, provided herein is a polymeric nanoparticle comprising
  a) a TNF-α protein comprising the amino acid sequence at least 70% identical to the sequence of SEQ ID NO: 9, or a portion thereof, or an isolated nucleic acid that encodes a TNF-α protein comprising the amino acid sequence at least 70% identical to the sequence of SEQ ID NO: 9, or a portion thereof; and
  b) one or more chemotherapeutic agents or a targeted anti-cancer agent.

In an embodiment, the chemotherapeutic agent or a targeted anti-cancer agent selected from the group consisting of doxorubicin, daunorubicin, decitabine, irinotecan, SN-38, cytarabine, docetaxel, triptolide, geldanamycin, 17-AAG, 5-FU, oxaliplatin, carboplatin, methotrexate, paclitaxel, indenoisoquinolines, and bortezomib Although the subject matter has been described in considerable detail with reference to certain embodiments thereof, other embodiments are possible. As such, the spirit and scope of the appended claims should not be limited to the description of the specific embodiments contained therein.

EXAMPLES

The disclosure will now be illustrated with working examples, and which is intended to illustrate the working of disclosure and not intended to restrictively any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Example 1: Flow Cytometry Analysis of GFP Expression

Reporter plasmid DNA expressing Green Fluorescent Protein (pEGFP N3) was used in complex formation to analyze the transfection efficiency of nanocomplexes and nanoparticles. After transfection with NC-GFP, PD-GFP and PPD-GFP; MCF-7 cells were analyzed at different time points of 0.5, 1, 2, 3, 4, 5 and 6 days. Here cells were trypsinized (100 µl of 0.25% trypsin) and washed with ice cold 1×PBS and re-suspended in 200 µl of 1× phosphate buffered saline (PBS). Measurements were carried out by Aria-III Flow Cytometer (San Jose, Calif.). The expression of Green Fluorescent Protein was observed at an excitation of 488 nm and 50,000 events were acquired in each case. The data show the average of three independent experiments.

Example 2: Cell Viability

The toxic effects of nanocomplexes and nanoparticles were measured using a thiazolyl blue tetrazolium bromide (MTT) assay. Human breast adenocarcinoma cell line MCF-7 cells were seeded at 6000 cells per well in 96-well plate format. After 24 hours, cells were treated with NC-GFP, PPD-GFP and Invitrogen Lipofectamine 2000™ at a pDNA concentration of 8 μg for 4 hours. Cell viability was assayed after 1, 2, 3 and 4 days after transfection. Briefly, a volume (50 μL) of MTT reagent (0.5 mg/mL) was added to each well. The plate was incubated at 37° C. for 15 minutes such that cell lysis was achieved. The medium containing the MTT reagent was decanted carefully from the wells such that the crystals were not detached. Following incubation, 100 μL of MTT detergent buffer (0.5 mL of 10% SDS and 0.06 mL of 12 N HCl in 10 mL of isopropanol) was added to each well, and crystals were dissolved by gentle shaking for 30 minutes. Absorbance analysis was performed at 550 and 670 nm (to negate debris). The percentage viability was calculated as shown below:

$$\frac{\text{Treated well } (OD_{550} - OD_{670})}{\text{Untreated well } (OD_{550} - OD_{670})} \times 100$$

The average of two independent experiments was plotted and each treatment was performed in quadruplicate.

Example 3: Western Blotting

After transfection with various formulations, cells were lysed in 50 μl radioimmunoprecipitation assay (RIPA) buffer and were re-suspended in 50 μl 2× sodium dodecyl sulfate (SDS) sample buffer with 1% β-mercaptoethanol. Samples were boiled for 5 minutes and separated on a 12% SDS-PAGE electrophoresis gel (20 μl per lane). After electrophoresis, the proteins were transferred to a polyvinylidene difluoride (PVDF) membrane (Millipore; Billerica, Mass.) using wet transfer cell system (Bio-rad; Hercules, Calif.). The membrane was blocked for two hours in PBS containing 5% skim milk. TNF-α and caspase-3 expression were detected by incubating the membrane with a primary antibody, rabbit anti-human TNF-α and rabbit anti-human caspase-3 respectively (1:2000 dilution, Abcam; Cambridge, United Kingdom) overnight at 4° C. The primary antibody solutions were discarded and the membrane was incubated for two hours with a solution containing a secondary antibody enzyme horseradish peroxidase (HRP)-labeled goat anti-rabbit IgG antibody (1:1000 dilution, Abcam). The TNF-α protein and caspase-3 protein were detected by enhanced chemiluminescence (ELC, Thermo Scientific™ Pierce; Lenexa, Kans.). An anti-glyceraldehyde 3-phosphate dehydrogenase (GAPDH) monoclonal antibody (Santa Cruz Biotechnology; Dallas, Tex.) was used as a protein loading control.

Example 4: Annexin-V Staining

The functional effect of TNF-α encoding plasmid DNA on cells was analyzed by Annexin-V staining (Thermo Scientific™ Pierce). Human breast adenocarcinoma MDA-MB-231 cells were transfected with TNF-α pDNA loaded PPD-TNF-α nanoparticles. After 24, 48 and 72 hours the treated cells were washed with 1×PBS and were collected after trypsinization. The trypsinized cells were centrifuged at 600 revolutions per minute (rpm) for ten minutes. The cell pellet was re-suspended in Annexin-V buffer and stained for 15 minutes with fluorescein isothiocyanate (FITC) labeled Annexin-V and propidium iodide (PI). After incubation cells were analyzed on Aria-III Flow cytometer (Thermo Scientific™ Pierce).

Example 5: Immunocytochemistry

Confocal laser scanning microscopy (CLSM) was employed to investigate the gene expression and its functional effect in-vitro on MDA-MB-231 cells. For CLSM observation, the cells were seeded in 35 millimeter (mm) μ-dishes at a density of $1 \times 10^5$ cells per dish. After incubation at 37° C. for 24 hours, cells were transfected with PPD-TNF-α. After 12 hours, the medium was removed and fresh medium was added. After 24, 48 and 72 hours, the medium was removed and cells were washed with 1×PBS three times. Thereafter, the cells were incubated with TNF-α primary antibody or a caspase-3 primary antibody for one hour and then with FITC and cyanine 5 (Cy5) fluorophore-labeled secondary antibody for one hour. The cells were then washed with PBS and cell nuclei were stained with a Hoechst 33258 dye (Thermo Scientific™ Pierce). The cells were then incubated with 200 μl 1×PBS for CLSM observation.

Example 6: In-Vivo Studies

Female syngeneic BALB/c mice, 10-12 weeks age (~22-25 grams of weight) were used in this in vivo analysis. The subjects were kept under pathogen free conditions according to Association for Assessment and Accreditation of Laboratory Animal Care International (AAALACI) guidelines and were acclimatized for four days prior to any testing. Animals were humanely cared for and supplied with food and water ad libitum. All animal experiments and study protocol were performed at All India Institute of Medical Science (AIIMS) New Delhi as per institutional guidelines and approved by the Committee for the Purpose of Control and Supervision of Experiments on Animals (CPCSEA) Government of India, New Delhi.

Example 7: Ehrlich Ascites Tumor (EAT) Model

EAT cells were maintained in the peritoneum of the mice in ascites form by serial weekly passage. Exponentially growing EAT cells were harvested, washed and re-suspended in PBS. An amount of the EAT cells (~$1.8 \times 10^6$ cells/mice) was injected subcutaneously (s.c.) in the thigh of the right hind leg of each subject.

Example 8: Maximum Tolerated Dose (MTD) Studies

Single intraperitoneal (IP) delivery of PPD-TNFα nanoparticles was performed in healthy female syngeneic BALB/c mice to study MTD. Five groups of five syngeneic BALB/c mice received single IP injections of PPD-TNFα nanoparticles with different pDNA-TNF-α concentration (0.6 mg/kg, 1.2 mg/kg, 1.8 mg/kg and 2.4 mg/kg of pDNA per dose). PBS was utilized as a control. Mice survival and variation in body weight were measured daily for 15 days. The MTD was defined as the allowance of a median body weight of 15% of the control that caused neither death due to toxic effects nor remarkable changes in the general signs within one week after administration. Animals showing weight loss exceeding 20% were sacrificed, as changes of this magnitude often indicated lethal toxicity.

Example 9: In-Vivo Tumor Regression Analysis

In the subcutaneous EAT model, treatments were started when a tumor in the syngeneic BALB/c mice reached a tumor volume ~50 mm$^3$ and this day was designated at day 0. On day 0, these mice were randomly divided into 5 groups (n=6). The starting time of treatment was considered as day 1 after tumor implantation (tumor volume of approximately ~50 mm$^3$) and continued for 50 days. Mice were administered intraperitoneally or intratumorally (IT) with bare plasmid DNA (pDNA-TNF-α), peptide-plasmid DNA nanocomplexes (NC-TNF-α) and polymer-peptide-plasmid DNA nanoparticles (PPD-TNF-α) on day 1, 5, 9, 13, 17 and 21. PPD-TNF-α nanoparticles were administered either of two pDNA doses (0.6 mg/kg and 1.2 mg/kg) for comparison. Bare pDNA-TNFα and NC-TNF-α were examined at a pDNA concentration of 14 µg. The mice in the control group were administered PBS only. Tumor sizes were measured with a venire caliper twice a week. Tumor volume was calculated by the formula $(L \times W^2)/2$, in which L is the longest and W is the shortest diameter (mm) of the tumor. On the third day of the last dosage, blood samples were obtained from all mice for measurement of blood cell counts, alanine aminotransferase (ALT), aspartate aminotransferase (AST), total bilirubin, blood urea nitrogen (BUN) and creatinine. One mouse from each group was also sacrificed and the tumor, heart, liver, kidney, spleen and lung taken for histopathology evaluation.

Example 10: Histological Analysis

The tissues samples (heart, lung, liver, spleen, kidney and tumor) of treated mice were taken for histopathological analysis. The samples were embedded in paraffin and then five micrometer (µm, micron) dimension sections were prepared. These sections were stained with hematoxylin-eosin (H&E) stain and were analyzed using a microscope.

Example 11: Fluorescence-Activated Cell Sorting (FACS) Analysis of Tumor Sections The tumor sections of sacrificed mice were analyzed for the presence of antitumor protein TNF-α and the apoptotic cascade protein caspase-3. Tumor sections were chopped and treated with lysis buffer for 5 minutes. The treated sections were then homogenized in a manual homogenizer for 5 minutes. The homogenized tumor sections were centrifuged and the supernatant from each sample was collected. The extracted supernatant was incubated with fluorescent antibodies against TNF-α and caspase-3 for 30 minutes. Treated supernatant were then analyzed by FACS for the respective antitumor protein.

Example 12: Generation of Peptide Sequence CR5H7R4C

The C-cyclized polycationic peptide CR$_5$H$_7$R$_4$C (amino acid sequence CRRRRRHHHHHHHRRRRC; >95% purity) was synthesized (G L Biochem Ltd; Shanghai, China). Peptides were dissolved in de-ionized water at a concentration of 5 mg/ml and stored in small aliquots at −80° C. to avoid repeated freeze-thaw. The plasmids pEGFP-N3 (Clontech; Mountain View, Calif.) and pE425-TNF-α were purified using a GenElute HP endotoxin free plasmid Maxiprep kit (Sigma-Aldrich; St. Louis, Mo.). A PLA-PEG block co-polymer of 75 kilodaltons (kDa) was designed and synthesized. See Kumar et al. Cancer Research, 2014 74(12): 3271-3281. Primary and secondary antibodies for TNF-α, caspase-3 and GAPDH were obtained (Abcam Pvt Ltd.; Cambridge, United Kingdom). All the chemicals used were purchased from Sigma-Aldrich (St. Louis, Mo.) unless stated otherwise.

Example 13. Preparation of Peptide-Plasmid DNA Complex (Nanocomplexes)

Peptide-pDNA nanocomplexes (NC) were prepared on the basis of electrostatic interaction in a ratio of amino nitrogen ($NH_3^+$) of peptide per phosphate ($PO_4^-$) group of DNA and designated as charge ratio (Z(±)). The pDNA stock was diluted to a concentration of 20-40 ng/µL and added drop wise to an equal volume of the appropriate peptide dilution while vortexing. In this Example, the nanocomplexes were prepared at a charge ratio Z(±) of 10.0.

Example 14. Preparation of PLA-PEG-Peptide-pDNA Based Nanoparticles (NP)

The PLA-PEG-Peptide-pDNA nanoparticles were prepared using a double emulsion evaporation method. Polymer solution and surfactant were prepared as: a) PEG-PLA block co-polymer was dissolved in acetonitrile at a concentration of 6 mg/ml and b) Ploxomer F-127 was dissolved at 3 mg/ml concentration in de-ionized water with continuous stirring to prepare surfactant solution. A fresh batch of peptide-pDNA nanocomplexes were prepared as described above and then gently mixed with the PLA-PEG solution and then added slowly into the aqueous surfactant solution. This solution was kept at a continuous stirring for approximately twelve hours to form stable nanoparticle solution. These N/Ps were prepared in three sets: i) only polymer N/Ps (NP), ii) polymer-pDNA N/Ps (PD), iii) polymer-peptide-pDNA N/Ps (PPD). The N/Ps materials were stored at −80° C. The pE425-TNFα plasmid was used in place of reporter plasmid DNA in preparation of PPD nanoparticles to study the antitumor effect of plasmid DNA loaded nanoparticles. The nanocomplexes and nanoparticles were prepared with reporter plasmid DNA (pEGFP-N3) are NC-GFP, PD-GFP and PPD-GFP. Nanocomplexes and nanoparticles prepared with anti-tumor protein TNF-α encoding plasmid DNA (pE425-TNFα; Clontech Laboratories Inc., California) are NC-TNF-α, PD-TNF-α and PPD-TNF-α.

Example 15. Biophysical Characterization

Size and zeta potential of nanocomplexes and polymeric nanoparticles were measured using a Zetasizer Nano ZS system (Malvern Instruments; Malvern, United Kingdom) at a fixed angle of 173° at 25° C. A minimum of three readings were recorded for each sample. Replicates were also analyzed. The morphology of nanocomplexes and nanoparticles was imaged by transmission emission microscopy (TEM). The release pattern of pDNA from nanoparticles was analyzed by incubating the nanoparticles in physiological buffer (1×PBS). After every one hour the solution was centrifuged, supernatant was collected and analyzed for the presence of pDNA. The pellet was then again suspended in PBS. The supernatant was treated with ten micrograms per microliter (µg/µl) heparin for ten minutes and then analyzed using an ethidium bromide (EtBr) exclusion assay.

Example 16. In-Vitro Transfection

MCF-7 and MDA-MB-231 cells were cultured in Dulbecco's Modified Eagle Medium (DMEM), supplemented with 10% (v/v) fetal bovine serum (Life Technologies/Thermo Scientific™ Pierce; Lenexa, Kans.) at 37° C. and 5% carbon dioxide in a humidified incubator. Cells were seeded in a 24-well plate format and the in-vitro experiments were carried out after 24 hours when a confluence of 70% was reached. Nanocomplexes were prepared at a charge ratio of 10.0 and incubated for an hour. A 100 microliters (µl) volume of nanocomplexes (2 µg of pDNA/well) were added to the cells with 300 µl of serum free medium (OptiMEM//Thermo Scientific™ Pierce; Lenexa, Kans.). Nanoparticles (PD-GFP and PPD-GFP) were added to the cells in an increasing concentration of pDNA per well as 2 micrograms (µg), 4 µg and 8 µg. To study the effect of serum on the transfection efficiency, the nanoparticles and nanocomplexes (at 8 µg pDNA/well) were added to the cells in the presence of 10% serum. The samples were incubated for twelve hours of incubation and then the medium containing nanoparticles and nanocomplexes was aspirated. The cells were rinsed with 1×PBS (pH 7.4) and supplemented with complete growth medium.

Example 17. Generation of Novel Dual NP/NCs

Systemic administration of vectors encoding cytokines is a potential approach for reprogramming of the intratumoral immune microenvironment. However, this field has been limited by the lack of effective delivery systems (Yin H et al., 2014 Nature Reviews Genetics 15, pages 541-555; Amer M. H., 2014 Mol Cell Ther. 2014; 2: 27, pages 1-19; Collins M. et al., 2015 Proc. Biol. Sci. 22; 282(1821):20143003. doi: 10.1098/rspb.2014.3003). To address this obstacle, Examples developed a dual system that includes an outer polymeric PLA-PEG nanoparticle (NP) that surrounds a cationic particle containing a peptide-DNA vector nanocomplex (NC). The histidine and cysteine modified arginine peptide (HCR) component of the NC has been designed for maintaining the balance of DNA condensation and intracellular release (Mann A. et al., 2014 Mol. Pharmaceutics, 11 (3), pages 683-696).

Three sets of nanoparticles i) unloaded polymeric nanoparticles (NP), ii) pDNA loaded polymeric nanoparticles (PDNPs) and iii) peptide-DNA nanocomplexes loaded polymeric nanoparticles (NP/NCs) were prepared by the nanoprecipitation method using PLA-PEG block copolymer (molecular weight of 75 KDa). See Shi J. et al., 2013 J. Bio Eng., 7:25; pages 1-10. All the three sets of nanoparticles were compared with peptide-pDNA nanocomplexes (NC) for their biophysical, in vitro and in vivo characterizations. The hydrodynamic diameter and polydispersity index values of the synthesized nanocomplexes and nanoparticles were analyzed in deionized water and serum (See FIG. 1A and FIG. 1B). Peptide-pDNA nanocomplexes (NC) were monodisperse with a size range of 80±4 nm, while pDNA-polymer nanoparticles were more than double the size (250±7 nm) in deionized water. The zeta potential of PLA-PEG NPs was determined to be −30 mV as measured using a Zetasizer Nano ZS system. Peptide-pDNA nanocomplexes (NC) however showed positive zeta potential of +25 mV.

Figures 1A, 1B:
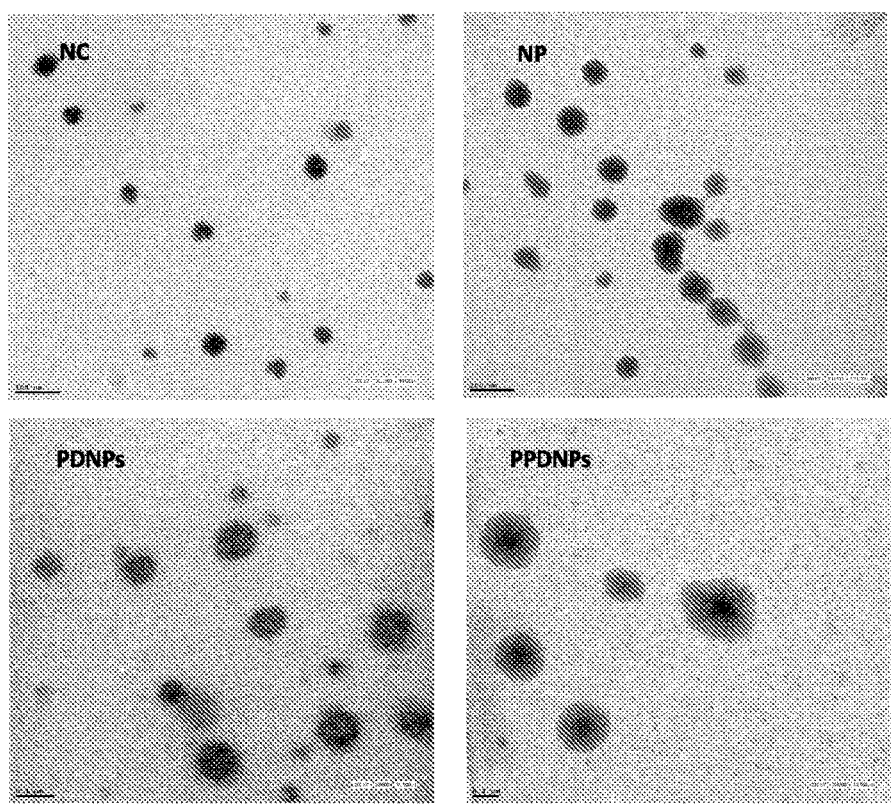
FIG. 1A is a table showing the hydrodynamic diameter (nanometer; nm) of different nanoparticles. The hydrodynamic diameter for each nanoparticle was determined using dynamic light scattering (DLS) in non-physiological buffer (PBS pH 7.4).
FIG. 1B is a transmission electron microscopy (TEM) image of peptide-pDNA nanocomplexes and nanoparticles. The nanoparticles imaged include peptide-pDNA nanocomplexes (NC), unloaded polymeric nanoparticles (NP), pDNA loaded polymeric nanoparticles (PDNPs) and PLA-PEG nanoparticles (PPD-NPs). The scale is 100 nm.
Figure 1C:
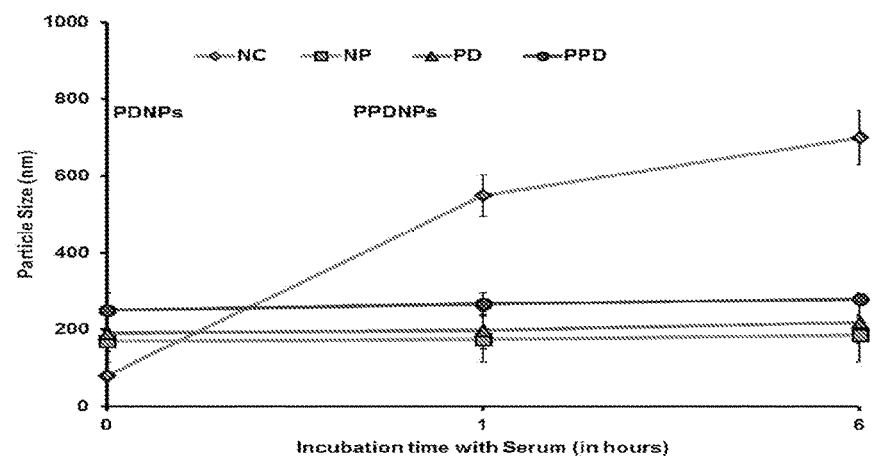
FIG. 1C is a set of graphs showing the hydrodynamic diameter of nanoparticles when challenged with serum. The hydrodynamic diameter was determined by DLS (nm).

Transmission electron micrographs of polymeric nanoparticles are shown in FIG. 1B and the images demonstrate that the nanoparticles were spherical in shape. In presence of serum, the NC showed polydisperse sizes in a range from 200 to 700 nm, indicating that the aggregation and the destabilization of the nanocomplexes. PLA-PEG nanoparticles (PPDNPs) containing peptide-pDNA nanocomplexes were observed to be stable in size without any aggregation even in presence of serum (see FIG. 1C). Polymer-pDNA (PD) and Polymer-Peptide-pDNA (PPD) nanoparticles were evaluated for pDNA loading efficiency. The loading efficiency of pDNA in PDNPs and PPDNPs was approximately 40% and 60% respectively.

Without being limited by any particular theory or mechanism of action, it is here envisioned that the observed lesser amount of loading of pDNA in PLA-PEG nanoparticles may be due to the repulsive action of the negatively charged PLA-PEG and pDNA, while peptide-pDNA nanocomplexes were positively charged and thus, were encapsulated in a higher percentage in negatively charged PLA-PEG polymeric nanoparticles.

Example 18. Release Kinetics of Peptide-DNA from Polymeric Nanoparticles

Figure 1D:
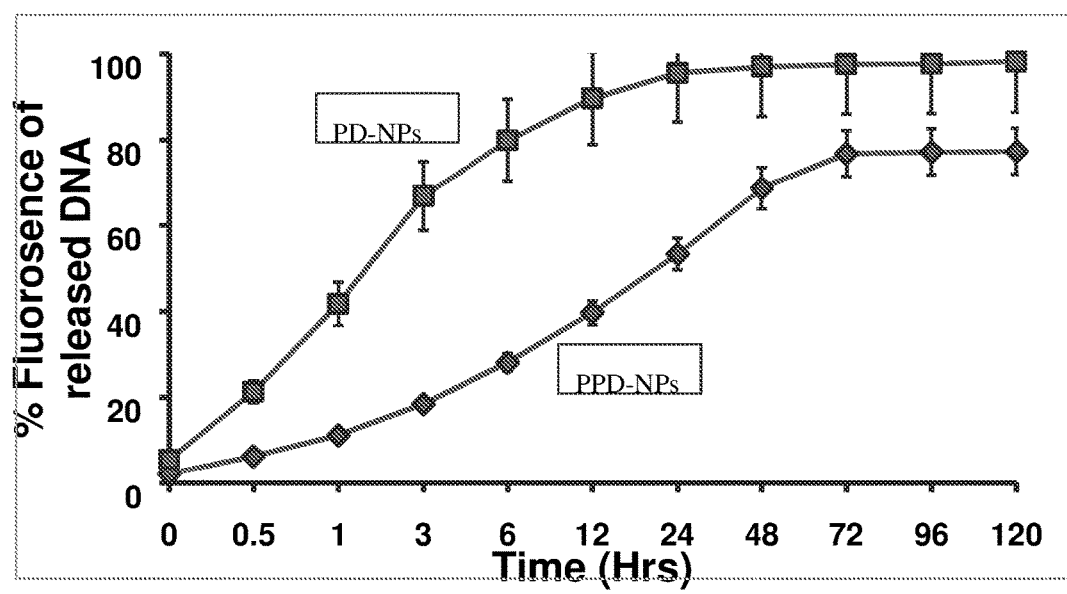
FIG. 1D is a graph showing release kinetics of nanoparticles in phosphate buffered saline (PBS). The graph shows percent fluorescence of released DNA (ordinate) of pDNA loaded polymeric nanoparticles (PDNPs) and PLA-PEG nanoparticles (PPD-NPs) over time in hours (abscissa; hrs).

PDNPs and PPDNPs were analyzed for their pDNA release kinetics in a physiological condition (1×PBS) using an EtBr exclusion assay. Approximately 60% of pDNA was released from PD nanoparticles within three hours, whereas PPD released pDNA in a gradual manner with a cumulative pDNA release of 30%, 45% and 60% for 12 hours, 24 hours and 48 hours respectively (FIG. 1D). The mechanism of pDNA release from the PLA-PEG-Peptide-pDNA nanoparticles (PPD) was observed to occur in two phases, i.e. a burst release phase and controlled release phase. In the burst release phase, a 20% release occurred in the first four hours, corresponding to the peptide-pDNA nanocomplexes being adsorbed or attached by weak bonding onto the surface of the nanoparticles. In the controlled release phase, the PPD nanoparticles were observed to have a gradual release of pDNA for up to 48 hours, which may occur because of the slow degradation of high molecular weight PLA-PEG block copolymer. Without being limited by any particular theory or mechanism of action, it may be that this observation can be extrapolated to the expression pattern of the pDNA in the cellular system, such that the more the sustained release of pDNA, the longer and higher the expression in in-vitro conditions. In case of PDNPs, the pDNA release phenomenon was observed to be faster than the release observed from PPDNPs, i.e. 60% within three hours due to repulsion between negative charges of pDNA and PLA-PEG nanoparticles. The pDNA was condensed with cationic peptides to form nanocomplexes, thus reducing the size and masking the charge of pDNA, which resulted in higher loading of NCs in (PPDNPs).

Accordingly, data show that release of the HCR-DNA complexes from the dual NP/NCs was sustained over 48 hours under physiologic conditions, supporting the potential for delivery of exogenous genes.

Example 19. Intracellular Expression of Peptide-GFP cDNA Complexes

Figure 2A:
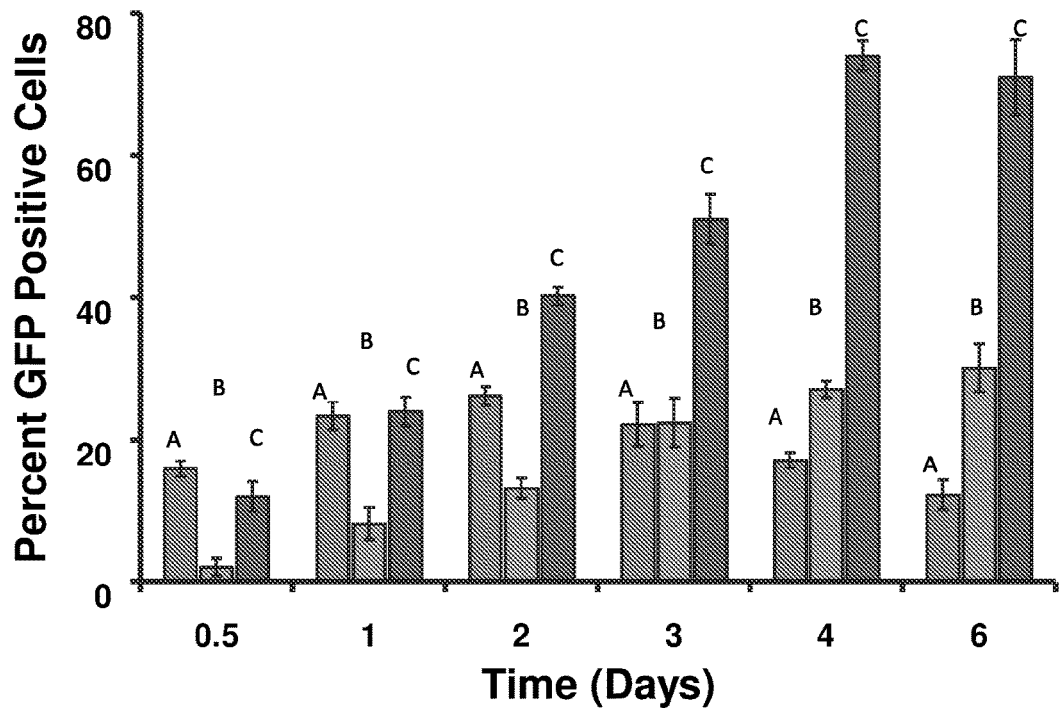
FIG. 2A is a graph showing green fluorescent protein (GFP) expression in MCF-7 cells after transfection with NC-GFP (columns A), PD-GFP (column B) and PPD-GFP (columns C) in presence of 10% serum. The percentage of cells expressing GFP (ordinate) was analyzed over days (abscissa). Time kinetics expression pattern of GFP for NC-GFP, PD-GFP and PPD-GFP was examined for 6 days.
Figure 2B:
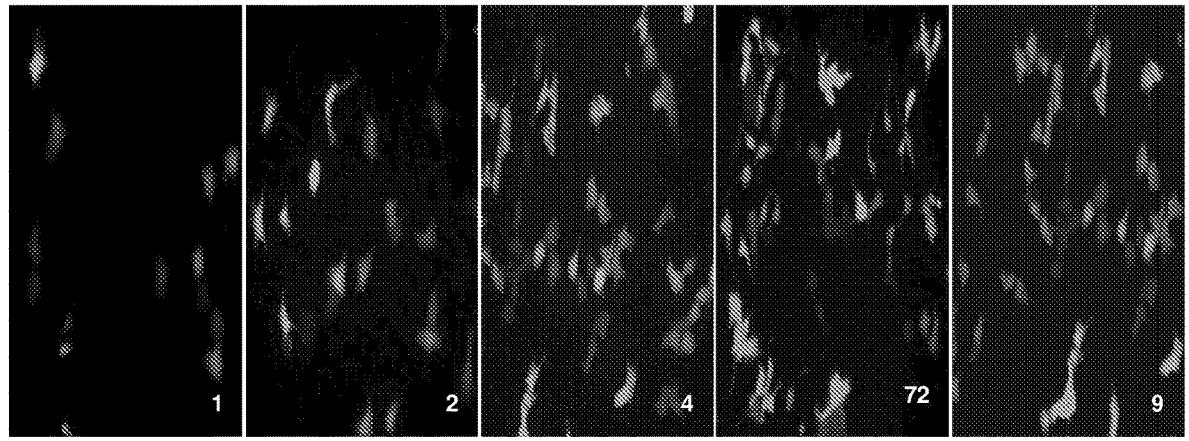
FIG. 2B is a set of photomicrographs showing qualitative analysis of the GFP expression pattern of MCF-7 cells treated with PPD-GFP nanoparticles over time (i.e. after 24 hours, 48 hours, 72 hours and 96 hrs).
Figure 2C:
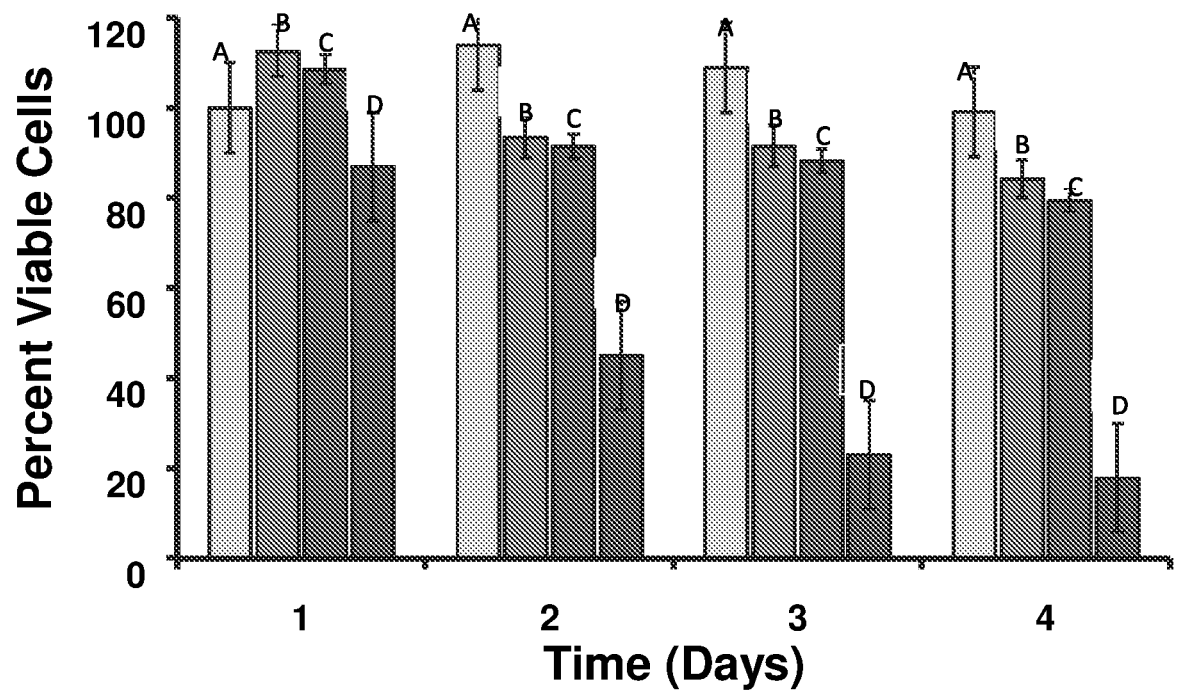
FIG. 2C is a graph analyzing cytotoxicity after transfection with NC-GFP and PPD-GFP, of MCF-7 cells over time as compared to cytotoxicity for cells treated with Invitrogen Lipofectamine 2000™ only. The graph shows percent of viable cells (ordinate) after transfection with NC-GFP (columns B), PPD-GFP/NPs (column C), and lipofectamine only (column D). Data for untransfected cells are shown in column A.

To assess the intracellular expression of an exogenous gene, HCR peptide complexes were generated with the green fluorescence protein (GFP) cDNA (FIG. 2A). Exposure of MCF-7 cells to the NP/GFP-NCs was observed to result in a gradual increase in GFP expression over 96 hours (FIG. 2B). Moreover and notably, there was little if any effect of the NP/GFP-NCs on cell viability, a finding in contrast to transfection of the GFP-NCs in the presence of Lipofectamine (see FIG. 2C).

Figure 4A:
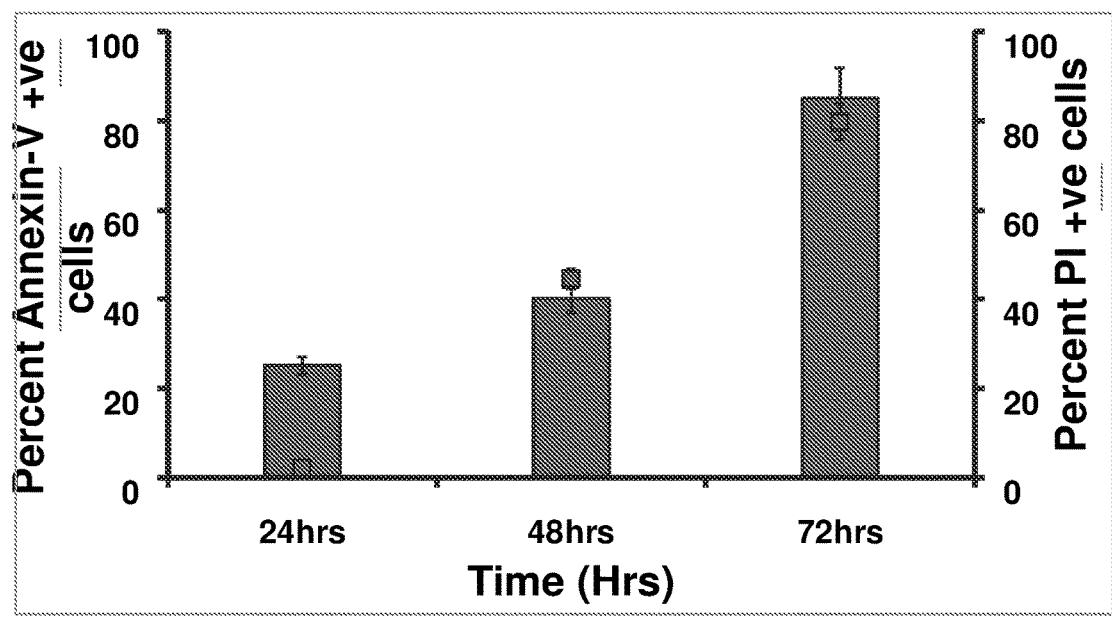
FIG. 4A is a graph showing percentage of Annexin V positive MCF-7 cells (ordinate) over time (abscissa) for PPD-TNF-α treated cells. Data show Annexin-V staining for apoptotic MCF-7 cells after 24, 48 and 72 hours.
Figure 4B:
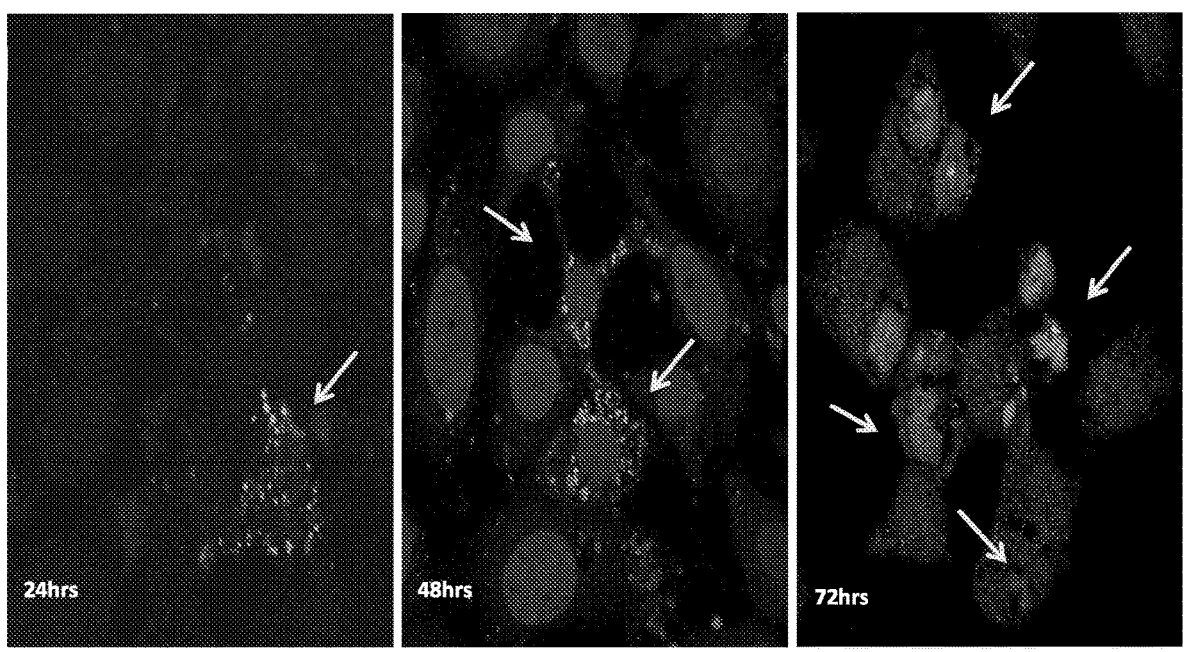
FIG. 4B is a set of photomicrographs showing immunocytochemistry analysis of TNF-α and caspase-3 after treating MCF-7 cells with PPD-TNFα/NPs at different time intervals: 24 hours, 48 hours and 72 hours.
Figure 4C:
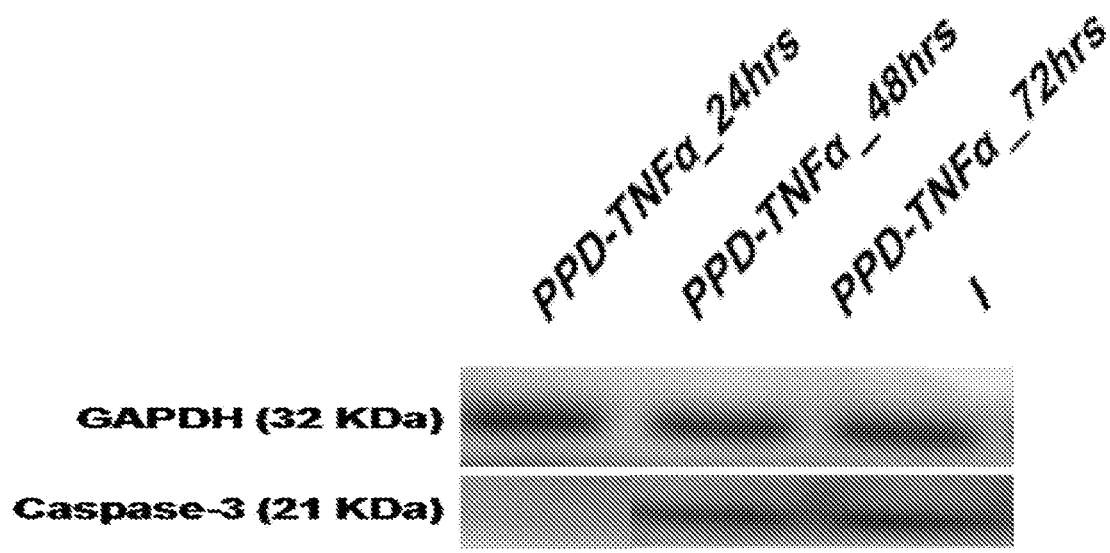
FIG. 4C is a photograph of a Western blot of caspase-3 protein expressed in TNF-α expressing MCF-7 cells which were transfected by TNF-α pDNA encapsulating NC-TNFα and PPD-TNF-α. Immunostaining images show presence of TNF-α and caspase-3 in PPD-TNFα transfected cells after 24 hours, 48 hours and 72 hrs.

Example 20. Generation of NP/NCs as a Model for In Vitro Induction of TNF Expression and Apoptosis An expression vector was constructed in which the human TNF cDNA is driven by a reactive oxygen species (ROS)-inducible promoter (pE425) derived from the EGR1 gene (Weichselbaum R. et al., 2009 Cancer Gene Therapy 16, pages 609-619). For a model system, NCs were generated containing HCR peptide linked to the pE425-TNF cDNA (TNF-NCs) (FIG. 3A). The TNF-NCs were then encapsulated in PLA-PEG NPs (NP/TNF-NC) (FIG. 3B). Significantly, treatment of MCF-7 cells with the NP/TNF-NCs was associated with expression of the TNF transmembrane (21 kDa) and soluble (17 kDa) proteins (FIG. 3B). In contrast to NP/GFP-NCs, treatment with the NP/TNF-NCs was effective in inducing cell death (FIG. 3C). Western blot analysis was also performed. Data show caspase-3 protein was expressed in TNFα expressing cells which were transfected by TNFα pDNA encapsulating NC-TNFα and PPD-TNFα. Immunocytostaining data show presence of TNFα and caspase-3 in PPD-TNFα transfected cells after 24, 48 and 72 hrs. Analysis of Annexin V staining data showed that MCF-7 cells responded to NP/TNF-NCs such that the cells were directed to apoptosis (FIG. 4A). In concert with these data, it was also observed that induction of intracellular TNF expression was associated with activation of caspase-3 cleavage as determined by immunocytochemistry analysis (FIG. 4B) and immunoblot analysis (FIG. 4C).

Example 21. Anti-Tumor Activity of NP/TNF-NCs In Vivo

Figure 5:
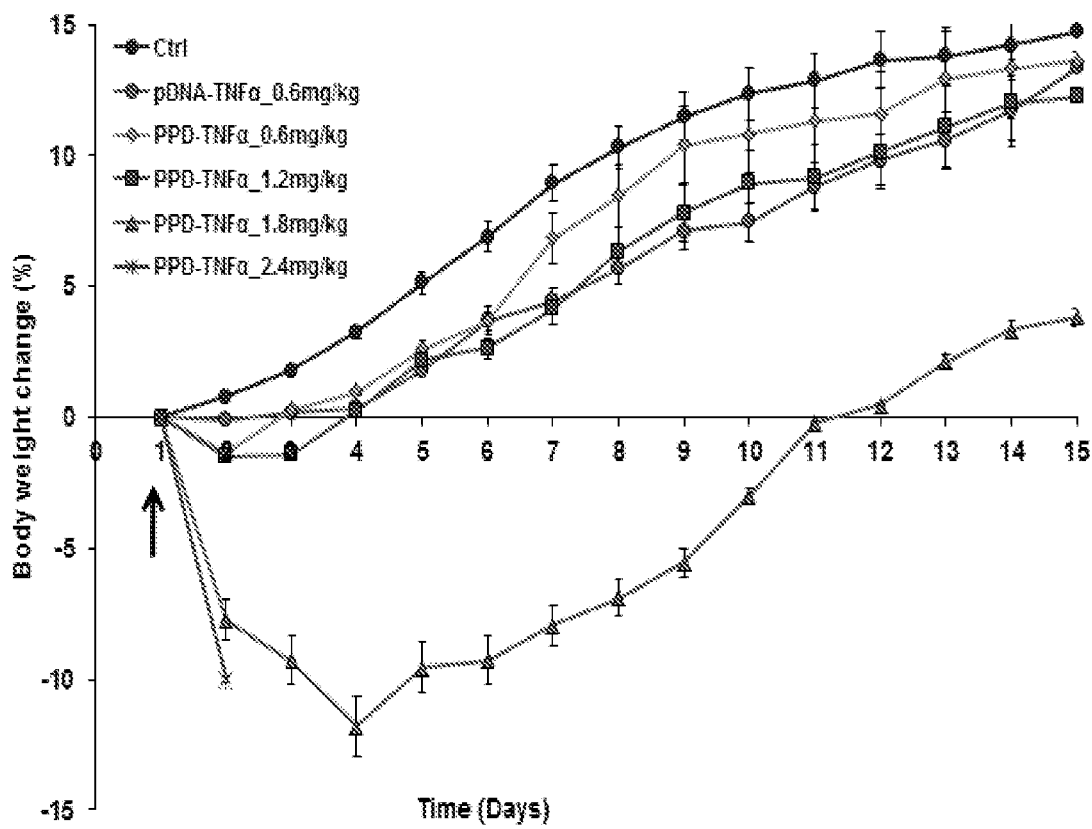
FIG. 5 is a graph showing percent body weight change (ordinate) of groups of BALB/c mice (five mice per group) intraperitoneally administered a single dose of PPD-TNF-α nanoparticles with different pDNA-TNF-α concentrations (0.6 mg/kg, 1.2 mg/kg, 1.8 mg/kg or 2.4 mg/kg) PPD-TNF-α nanoparticles.

Tolerability of NP/TNF-NCs was first analyzed by intraperitoneal (IP) administration in BALB/c mice. Data show that single NP/TNF-NC doses of 0.6 and 1.2 mg/kg were well tolerated without significant weight loss or other overt signs of toxicity (FIG. 5). In contrast, administration of NP/TNF-NC at a dose of 1.8 mg/kg was associated with weight loss of >10% that recovered by day 7 (FIG. 5).

Based on these data, the effects of NP/TNF-NCs in mice bearing established Ehrlich breast tumors were analyzed. Notably, multiple IP administration of NP/TNF-NCs at doses of 0.6 and 1.2 mg/kg×6 was associated with inhibition of tumor growth (FIG. 6A). Moreover, tumor regrowth was detectable by day 50 (FIG. 6B). For comparison, the effects of intratumoral (IT) administration were also analyzed. Growth inhibitory effects were observed when the NP/TNF-NCs were administered intratumorally at a dose of 0.6 mg/kg×6 (FIG. 7A). Moreover, it was observed that increasing the IT dose to 1.2 mg/kg×6 resulted in tumor regression that persisted through day 50 (FIG. 7A and FIG. 7B). Significantly, there was no evidence of organ toxicity or blood chemistry abnormalities associated with NP/TNF-NC treatment (FIG. 8 and Tables 3 and 4).

TABLE 3

Hematology parameters of treated mice blood samples

| Parameters | Control | pDNA-TNFα | | NC-TNFα | | PPD-TNFα | |
|---|---|---|---|---|---|---|---|
| | | IT | IP | IT | IP | IT | IP |
| Hemoglobin (gm/dl) | 14.1 | 13.4 | 14.8 | 16.4 | 14.8 | 13.4 | 14.8 |
| Neutrophil (%) | 60 | 50 | 43 | 55 | 47 | 30 | 53 |
| Lymphocyte (%) | 38 | 45 | 39 | 36 | 35 | 35 | 29 |
| Eosinophil (%) | 4 | 3 | 6 | 6 | 4 | 2 | 4 |
| Monocyte (%) | 6 | 7 | 5 | 7 | 9 | 6 | 3 |
| RBC (millions/cmm) | 5.8 | 4.93 | 5.7 | 5.0 | 5.1 | 6.83 | 4.17 |
| Platelet counts (lakh/cmm) | 4.2 | 3.97 | 1.6 | 2.38 | 2.6 | 3.19 | 2.86 |

TABLE 4

Biochemical parameters of treated mice blood samples

| Parameters | Control | pDNA-TNFα | | NC-TNFα | | PPD-TNFα | |
|---|---|---|---|---|---|---|---|
| | | IT | IP | IT | IP | IT | IP |
| Blood Urea (mg/dl) | 28.3 | 39.5 | 35.3 | 23.8 | 24.1 | 32.4 | 44 |
| Serum Creatinine (mg/dl) | 0.6 | 0.8 | 0.4 | 0.6 | 0.5 | 1.1 | 0.99 |
| Blood Urea Nitrogen (BUN) (mg/dl) | 13.6 | 14.2 | 18.1 | 11 | 12 | 13 | 12.5 |
| SGOT (IU/L) | 39 | 60 | 28 | 15 | 18 | 29 | 36 |
| SGPT (IU/L) | 22 | 47 | 33 | 44 | 38 | 40 | 39 |
| Alkaline Phosphatase (U/L at 37° C.) | 64 | 66 | 53 | 83 | 88 | 64 | 78 |

Furthermore, analysis of tumor sections from the NP/TNF-NC-treated mice was also performed. An increased presence of apoptotic bodies was observed in tumors from NP/TNF-NC-treated mice as compared to control tumors (FIG. 9A). Moreover and importantly, IP and IT administration of NP/TNF-NCs resulted in a significant increase in TNF expression in tumor lysates that was associated with activation of caspase-3 (FIG. 9B). Without being limited by any particular theory or mechanism of action, it is here envisioned that NP/TNF-NCs may be effective against Ehrlich breast tumors when administered systemically or intratumorally.

Example 22: Preparation and Characterization of Polymeric Nanoparticles Formed of PLA-PEG-PPG-PEG Tetra-Block Copolymer (Also Described in PCT Publication No. WO2013/160773)

Poly(lactic acid) (Mw. ~45,000-72,000 g/mol), PEG-PPG-PEG (Table 1) and tissue culture reagents were obtained from Sigma-Aldrich (St. Louis, Mo.). All reagents were analytical grade or above and used as received, unless otherwise stated. Cell lines were obtained from NCCS Pune, India.

Preparation of PLA-PEG-PPG-PEG Block Copolymer 5 gm of poly (lactic acid) (PLA) with an average molecular weight of 60,000 g/mol was dissolved in 100 ml $CH_2Cl_2$ (dichloromethane) in a 250 ml round bottom flask. To this solution, 0.7 g of PEG-PPG-PEG polymer (molecular weight range of 1100-12,500 Mn) was added. The solution was stirred for 10-12 hours at 0° C. To this reaction mixture, 5 ml of 1% N,N-dicyclohexylcarbodimide (DCC) solution was added followed by slow addition of 5 ml of 0.1% 4-Dimethylaminopyridine (DMAP) at −4° C. to 0° C./sub-zero temperatures. The reaction mixture was stirred for the next 24 hours followed by precipitation of the PLA-PEG-PPG-PEG block copolymer with diethyl ether and filtration using Whatman filter paper No. 1. The PLA-PEG-PPG-PEG block copolymer precipitates so obtained are dried under low vacuum and stored at 2° C. to 8° C. until further use.

Preparation of PLA-PEG-PPG-PEG Nanoparticles

The PLA-PEG-PPG-PEG nanoparticles were prepared by emulsion precipitation method. 100 mg of the PLA-PEG-PPG-PEG copolymer obtained by the above mentioned process was separately dissolved in an organic solvent, for example, acetonitrile, dimethyl formamide (DMF) or dichloromethane to obtain a polymeric solution.

The nanoparticles were prepared by adding this polymeric solution drop wise to the aqueous phase of 20 ml distilled water. The solution was stirred magnetically at room temperature for 10 to 12 hours to allow residual solvent evaporation and stabilization of the nanoparticles. The nanoparticles were then collected by centrifugation at 25,000 rpm for 10 min and washed thrice using distilled water. The nanoparticles were further lyophilized and stored at 2° C. to 8° C. until further use.

Characterization of Polymeric Nanoparticles of PLA-PEG-PPG-PEG Block Copolymer

The shape of the nanoparticles obtained by the process mentioned above is essentially spherical as shown by Transmission Electron Micrsocopy Image. The TEM images allowed for the determination of the particle size range, which is about 30 to 120 nm. The hydrodynamic radius of the nanoparticle was measured using a dynamic light scattering (DLS) instrument and is in the range of 110-120 nm.

The NMR spectra of the PLA-PEG-PPG-PEG nanoparticles were obtained using different molecular weights of the block copolymer, PEG-PPG-PEG. In the spectra, proton with a chemical shift of about 5.1 represents the ester proton of PLA and the proton with a chemical shift at around 3.5 represent the ether proton of PEG-PPG-PEG. The presence of both the protons in the spectra confirms the conjugation of PLA with PEG-PPG-PEG.

Example 23: Preparation and Characterization of Peptide-pEGR-1-TNF DNA Encapsulated in Tetra Block Nanoparticles Polymeric nanoparticles comprising a tetra-block copolymer of PLA-PEG-PPG-PEG, and encapsulating peptide-pEGR-1-TNF DNA were prepared and characterized. Table 5 shows nanoparticle size and polydispersity index data using the different tetra block nanoparticles having two different molecular weights of PLA.

A comparison of TNF DNA release profiles in non-physiological PBS buffer pH 7.4 shows that each of the prepared tetra-block nanoparticles was an effective vehicle for gradual release of DNA (FIG. 10).

Further analysis was performed to compare the TNF DNA release profiles in non-physiological PBS buffer pH 7.4 using two different nanoparticles. Specifically, daily release of TNF-DNA from PLA 12 kDa-PEG-PPG-PEG peptide-TNF DNA nanoparticles and from PLA 72 kDa-PEG-PPG-PEG peptide-TNF DNA nanoparticles was analyzed (FIG. 11). In comparison to the daily release of TNF-DNA by using di-block (PLA-PEG) nanoparticles (described in Example 18, 100% DNA release completed in 120 hours or about 5 days), data here show that the tetra block (PLA-PEG-PPG-PEG) nanoparticles released 100% of TNF-DNA in 10 days (see FIGS. 10 and 11), such that there is a more gradual DNA release using the tetra-block nanoparticles.

TABLE 5

Particle Size and PDI of DNA loaded polymeric nanoparticles

| Sample | Particle Size (nm) | PDI |
|---|---|---|
| $PLA^{12KDa}$-PEG-PPG-PEG-DNA NPs | 110 ± 4 | 0.08 |
| $PLA^{12KDa}$-PEG-PPG-PEG-Pt-DNA NPs | 152 ± 8 | 0.05 |
| $PLA^{72KDa}$-PEG-PPG-PEG-DNA NPs | 180 ± 2 | 0.11 |
| $PLA^{72KDa}$-PEG-PPG-PEG-Pt-DNA NPs | 220 ± 4 | 0.09 |

We claim:
1. A composition comprising
   a) polymeric nanoparticles comprising poly(lactic acid)-poly(ethylene glycol)-poly(propylene glycol)-poly(ethylene glycol) (PLA-PEG-PPG-PEG) tetra-block copolymer; and
   b) an isolated nucleic acid encoding a protein comprising an amino acid sequence at least 95% identical to the amino acid sequence of SEQ ID NO: 9.

2. The composition of claim 1, wherein the PLA-PEG-PPG-PEG tetra-block copolymer is formed from chemical conjugation of PEG-PPG-PEG tri-block copolymer with PLA.

3. The composition of claim 1, wherein the molecular weight of PLA is between about 10,000 and about 100,000 daltons.

4. The composition of claim 1, further comprising a peptide comprising an amino acid sequence selected from the group consisting of SEQ ID NOs: 1, 2, 3, 4, 5, 6, 7, 8, and polyarginine, wherein the peptide and the isolated nucleic acid form a complex.

5. The composition of claim 1, further comprising a cationic cell-penetrating peptide.

6. The composition of claim 1, further comprising an agent selected from the group consisting of doxorubicin, daunorubicin, decitabine, irinotecan, SN-38, cytarabine, docetaxel, triptolide, geldanamycin, 17-AAG, 5-FU, oxaliplatin, carboplatin, methotrexate, paclitaxel, indenoisoquinolines, and bortezomib.

7. The composition of claim 1, wherein the polymeric nanoparticles further comprise a targeting moiety attached to the outside of the polymeric nanoparticles, and wherein the targeting moiety is an antibody, peptide, or aptamer.

8. The composition of claim 1, wherein the polymeric nanoparticle comprises a tetra-block copolymer selected from the group consisting of $PLA^{12kDa}$-PEG-PPG-PEG-DNA, $PLA^{12kDa}$-PEG-PPG-PEG-Pt-DNA, $PLA^{72kDa}$-PEG-PPG-PEG-DNA and $PLA^{72kDa}$-PEG-PPG-PEG-Pt-DNA.

9. The composition of claim 1, wherein the isolated nucleic acid comprises a nucleotide sequence at least 95% identical to nucleotides 404-874 of SEQ ID NO:11.

10. The composition of claim 1, wherein the isolated nucleic acid comprises nucleotides 404-874 of SEQ ID NO:11.

11. The composition of claim 1, wherein the isolated nucleic acid comprises a nucleotide sequence at least 95% identical to nucleotides 176-874 of SEQ ID NO:11.

12. The composition of claim 1, wherein the isolated nucleic acid comprises nucleotides 176-874 of SEQ ID NO:11.

13. The composition of claim 1, wherein the isolated nucleic acid comprises a nucleotide sequence at least 95% identical to the nucleotide sequence of SEQ ID NO:11.

14. The composition of claim 1, wherein the isolated nucleic acid comprises the nucleotide sequence of SEQ ID NO:11.

15. The composition of claim 1, wherein the isolated nucleic acid encodes the amino acid sequence of SEQ ID NO:9.

16. The composition of claim 1, wherein the isolated nucleic acid encodes an amino acid sequence at least 95% identical to the amino acid sequence of SEQ ID NO:10.

17. The composition of claim 1, wherein the isolated nucleic acid encodes the amino acid sequence of SEQ ID NO:10.

18. A pharmaceutical composition comprising
   a) polymeric nanoparticles comprising PLA-PEG-PPG-PEG tetra-block copolymer; and
   b) an isolated nucleic acid encoding a protein comprising an amino acid sequence at least 95% identical to the amino acid sequence of SEQ ID NO: 9.

19. The pharmaceutical composition of claim 18, wherein the PLA-PEG-PPG-PEG tetra-block copolymer is formed from chemical conjugation of PEG-PPG-PEG tri-block copolymer with PLA.

20. The pharmaceutical composition of claim 18, wherein the molecular weight of PLA is between about 10,000 and about 100,000 daltons.

21. The pharmaceutical composition of claim 18, further comprising a peptide comprising an amino acid sequence selected from the group consisting of SEQ ID NOs: 1, 2, 3, 4, 5, 6, 7, 8, and polyarginine, wherein the peptide and the isolated nucleic acid form a complex.

22. The pharmaceutical composition of claim 18, further comprising a cationic cell-penetrating peptide.

23. The pharmaceutical composition of claim 18, further comprising an agent selected from the group consisting of doxorubicin, daunorubicin, decitabine, irinotecan, SN-38, cytarabine, docetaxel, triptolide, geldanamycin, 17-AAG, 5-FU, oxaliplatin, carboplatin, methotrexate, paclitaxel, indenoisoquinolines, and bortezomib.

24. The pharmaceutical composition of claim 18, wherein the polymeric nanoparticles further comprise a targeting moiety attached to the outside of the polymeric nanoparticles, and wherein the targeting moiety is an antibody, peptide, or aptamer.

25. The pharmaceutical composition of claim 18, wherein the isolated nucleic acid comprises a nucleotide sequence at least 95% identical to nucleotides 404-874 of SEQ ID NO:11.

26. The pharmaceutical composition of claim 18, wherein the isolated nucleic acid comprises nucleotides 404-874 of SEQ ID NO:11.

27. The pharmaceutical composition of claim 18, wherein the isolated nucleic acid comprises a nucleotide sequence at least 95% identical to nucleotides 176-874 of SEQ ID NO:11.

28. The pharmaceutical composition of claim 18, wherein the isolated nucleic acid comprises nucleotides 176-874 of SEQ ID NO:11.

29. The pharmaceutical composition of claim 18, wherein the isolated nucleic acid comprises a nucleotide sequence at least 95% identical to the nucleotide sequence of SEQ ID NO:11.

30. The pharmaceutical composition of claim 18, wherein the isolated nucleic acid comprises the nucleotide sequence of SEQ ID NO:11.

31. The pharmaceutical composition of claim 18, wherein the isolated nucleic acid encodes the amino acid sequence of SEQ ID NO:9.

32. The pharmaceutical composition of claim 18, wherein the isolated nucleic acid encodes an amino acid sequence at least 95% identical to the amino acid sequence of SEQ ID NO:10.

33. The pharmaceutical composition of claim 18, wherein the isolated nucleic acid encodes the amino acid sequence of SEQ ID NO:10.

34. The pharmaceutical composition of claim 18, wherein the polymeric nanoparticle comprises a tetra-block copolymer selected from the group consisting of $PLA^{12kDa}$-PEG-PPG-PEG-DNA, $PLA^{12kDa}$-PEG-PPG-PEG-Pt-DNA, $PLA^{72kDa}$-PEG-PPG-PEG-DNA and $PLA^{72kDa}$-PEG-PPG-PEG-Pt-DNA.

* * * * *